United States Patent
Springer et al.

(10) Patent No.: US 6,683,158 B2
(45) Date of Patent: Jan. 27, 2004

(54) ALPHA-SUBUNIT OF THE MAC-1 LEUKOCYTE ADHESION RECEPTOR

(75) Inventors: Timothy A. Springer, Newton, MA (US); Angel Corbi, Madrid (ES)

(73) Assignee: Dana Farber Cancer Institute, Boston, MA (US)

( * ) Notice: Subject to any disclaimer, the term of this patent is extended or adjusted under 35 U.S.C. 154(b) by 0 days.

(21) Appl. No.: 10/147,873

(22) Filed: May 20, 2002

(65) Prior Publication Data

US 2003/0013850 A1 Jan. 16, 2003

Related U.S. Application Data

(63) Continuation of application No. 08/979,940, filed on Nov. 26, 1997, now abandoned, which is a division of application No. 08/433,801, filed on May 3, 1995, now Pat. No. 5,849,896, which is a continuation of application No. 08/077,098, filed on Jun. 16, 1993, now abandoned, which is a continuation of application No. 07/942,056, filed on Sep. 8, 1992, now abandoned, which is a continuation of application No. 07/321,239, filed on Mar. 9, 1989, now abandoned, which is a continuation-in-part of application No. 07/235,353, filed on Aug. 23, 1988, now abandoned.

(51) Int. Cl.[7] ............................................. C07K 14/705
(52) U.S. Cl. ...................................................... 530/350
(58) Field of Search ......................................... 530/350

(56) References Cited

U.S. PATENT DOCUMENTS

| | | |
|---|---|---|
| 4,761,371 A | 8/1988 | Bell et al. |
| 5,424,399 A | 6/1995 | Arnaout |
| 5,849,896 A | 12/1998 | Springer et al. |
| 2002/0022595 A1 | 2/2002 | Springer et al. |

OTHER PUBLICATIONS

Ed Gington Biotechnology 10:383–389 (1992).*
Ward Therapeutic Immunology 1:165–171 (1994).*
Kogan et al. J. Biol Chem. 270:14047–14055 (1995).*
Skolnick et al. Trends in Biotechnology 18:34–38 (2000).*
Anderson, D.C., et al., "Abnormalities of Polymorphonuclear Leukocyte Function Associated with a Heritable Deficiency of High Molecular Weight Surface Glycoproteins (GP138): Common Relationship to Diminished Cell Adherence," *J. Clin. Invest.* 74:536–552, American Society for Clinical Investigation, Inc. (1984).
Anderson, D.C., et al., "The Severe and Moderate Phenotypes of Heritable Mac–1, LFA–1 Deficiency: Their Quantitative Definition and Relation to Leukocyte Dysfunction and Clinical Features," *J. Infect. Dis.* 152:668–689, University of Chicago Press (1985).
Arnaout, M.A., et al., "Molecular cloning of the α subunit of human and guinea pig leukocyte adhesion glycoprotein Mo1: Chromosomal localization and homology to the α subunits of integrins," *Proc. Natl. Acad. Sci. USA* 85:2776–2780, National Academy of Sciences (Apr. 1988).

Arnaout, M.A., et al., "Amino Acid Sequence of the Alpha Subunit of Human Leukocyte Adhesion Receptor Mo1 (Complement Receptor Type 3)," *J. Cell Biol.* 106:2153–2158, Rockefeller University Press (Jun. 1988).
Beller, D.I., et al., "Anti–Mac–1 Selectively Inhibits the Mouse and Human Type Three Complement Receptor," *J. Exp. Med.* 156:1000–1009, Rockefeller University Press (1982).
Brian, A.A., and McConnell, H.M., "Allogeneic stimulation of cytotoxic T cells by supported planar membranes," *Proc. Natl. Acad. Sci. USA* 81:6159–6163, National Academy of Sciences (1984).
Bullock, W.E., and Wright, S.D., "Role of the Adherence–Promoting Receptors, CR3, LFA–1, and p150,95, in Binding of *Histoplasma capsulatum* by Human Macrophages," *J. Exp. Med.* 165:195–210, Rockefeller University Press (Jan. 1987).
Cerf–Bensussan, N., et al., "Immunohistologic and Immunoelectron Microscopic Characterization of the Mucosal Lymphocytes of Human Small Intestine by the Use of Monoclonal Antibodies," *J. Immunol.* 130:2615–2622, American Association of Immunologies (1983).
Clark,, E.A., and Yokochi, T., "Human B Cell and B Cell Blast–Associated Surface Molecules Defined with Monoclonal Antibodies," in *Leukocyte Typing I,* Bernard, A., et al., eds., Springer–Verlag, Berlin, pp. 339–346 (1984).
Clark, E., et al., "BB–2 Monoclonal Antibody Reactive with a B Cell–Associated Differentiation Antigen (B–p76) on Activated B Cells," in *Leukocyte Typing I,* Bernard, A., et al., eds., Springer–Verlag, Berlin, p. 740 (1984).
Clark, E.A., et al., "Polypeptides on Human B Lymphocyte Associated with Cell Activation," *Hum. Immunol.* 16:100–113, Elsevier Science Publishing Co., Inc. (1986).
Colonno, R.J., et al., "Characterization of the Cellular Receptor Specific for Attachment of Most Human Rhinovirus Serotypes," in *Virus Attachment and Entry Into Cells,* Crowell, R.L., ed., American Society for Microbiology, Washington, DC, pp. 109–115 (1986).
Corbi, A.L., et al., "The Human Leukocyte Adhesion Glycoprotein Mac–1 (Complement Receptor Type 3, CD11b) α subunit. Cloning, Primary Structure, and Relation to the Integrins, von Willebrand Factor and Factor B," *J. Biol. Chem.* 263:12403–12411, American Society for Biochemistry and Molecular Biology (Sep. 1988).

(List continued on next page.)

*Primary Examiner*—Phillip Gambel
(74) *Attorney, Agent, or Firm*—Sterne, Kessler, Goldstein & Fox, P.L.L.C.

(57) ABSTRACT

The present invention relates to Mac-1 alpha-subunit which is involved in the process through which cells recognize and migrate to sites of inflammation as well as attach to cellular substrates during inflammation. The invention is directed toward such molecules, the functional derivatives of such molecules, screening assays for identifying such molecules and therapeutic and diagnostic uses for such molecules.

4 Claims, 23 Drawing Sheets

OTHER PUBLICATIONS

Cunningham, B.A., et al., "Neural Cell Adhesion Molecule: Structure, Immunoglobulin–Like Domains, Cell Surface Modulation, and Alternative RNA Splicing," *Science* 236:799–806, American Association for the Advancement of Science (May 1987).

Dana, N., et al., "Two Functional Domains in the Phagocyte Membrane Glycoprotein Mo1 Identified with Monoclonal Antibodies," *J. Immunol.* 137:3259–3263, American Association of Immunologists (1986).

Davignon, D., et al., "Lymphocyte function–associated antigen 1 (LFA–1): A surface antigen distinct from Lyt–2,3 that participate in T lymphocyte–mediated killing," *Proc. Natl. Acad. Sci. USA* 78:4535–4539, National Academy of Sciences (1981).

Detmers, P.A., et al., "Aggregation of Complement Receptors on Human Neutrophils in the Absence of Ligand," *J. Cell Biol.* 105:1137–1145, Rockefeller University Press (Sep. 1987).

Dustin, M.L., et al., "Induction by IL 1 and Interferon–γ: Tissue Distribution, Biochemistry, and Function of a Natural Adherence Molecule (ICAM–1)," *J. Immunol.* 137:245–254, American Association of Immunologists (1986).

Dustin, M.L., et al., "Purified Lymphocyte Function–Associated Antigen 3 Binds to CD2 and Mediates T Lymphocyte Adhesion," *J. Exp. Med.* 165:677–692, Rockefeller University Press (Mar. 1987).

Edgington, S.M., "How Sweet It Is: Selectin–Mediating Drugs," *Biotechnology (NY)* 10:383–389, Nature Publishing Co. (1992).

Fischer, A., et al., "Role of the LFA–1 Molecule in Cellular Interactions Required for Antibody Production in Humans," *J. Immunol.* 136:3198–3203, American Association of Immunologists (1986).

Fischer, A., et al., "Prevention of Graft Failure by an Anti–HLFA–1 Monoclonal Antibody in HLA–Mismatched Bone–Marrow Transplantation," *Lancet* 2:1058–1061, Lancet (1986).

Gay, D., et al., "The Major Histocompatibility of Complex–Restricted Antigen Receptor on T Cells. IX. Role of Accessory Molecules in Recognition of Antigen Plus Isolated IA," *J. Immunol.* 136:2026–2032, American Association of Immunologists (1986).

Grossman, H.B., "Clinical Applications of Monoclonal Antibody Technology," *Urol. Clin. N. Amer.* 13:465–474, Saunders (1986).

Harlan, J.M., et al., "The Role of Neutrophil Membrane Glycoproteins GP–150 in Neutrophil Adherence to Endothelium In Vitro," *Blood* 66:167–178, Grune & Stratton (1985).

Haskard, D., et al., "T Lymphocyte Adhesion to Endothelial Cells: Mechanisms Demonstrated by Anti–LFA–1 Monoclonal Antibodies," *J. Immunol.* 137:2901–2906, American Association of Immunologists (1986).

Hickstein, D.D., et al., "cDNA sequence for the αM subunit of the human neutrophil adherence receptor indicates homology to integrin α subunits," *Proc. National Acad. Sci. USA* 86:257–261, National Academy of Sciences (1989).

Hogg, N., et al., "The p150,95 molecule is a marker of human mononuclear phagocytes: comparison with expression of class II molecules," *Eur. J. Immunol.* 16:240–248, Verlag Chemie GmbH (1986).

Hynes, R.O., "Integrins: A Family of Cell Surface Receptors," *Cell* 48:549–554, Cell Press (Feb. 1987).

Jones, D.H., et al., "Subcellular Location of Mac–1 (CR–3) in Human Neutrophils: Effects of Chemotactic Factors and PMA," *Ped. Res.* 21:312a (Abstract No. 835), Lippincott Williams & Wilkins (Apr.1987).

Katz, F.E., et al., "Chromosome mapping of cell membrane antigens expressed on activated B cells," *Eur. J. Immunol.* 85:103–106, Verlag Chemie GmbH (1985).

Keizer, G.D., et al., "Biochemical and functional characteristics of the human leukocyte membrane antigen family LFA–1, Mo–1, and p150,95," *Eur. J. Immunol.* 15:1142–1147, Verlag Chemie GmbH (1985).

Keizer, G.D., et al., "Membrane Glycoprotein p150,95 of Human Cytotoxic T Cell Clones Is Involved in Conjugate Formation with Target Cells," *J. Immunol.* 138:3130–3136, American Association of Immunologists (May 1987).

Keizer, G.D., et al., "Role of p150,95 in adhesion, migration, chemotaxis and phagocytosis of human monocytes," *Eur. J. Immunol.* 17:1317–1322, Verlag Chemie GmbH (Sep. 1987).

Khaw, B.A., et al, "Myocardial Infarct Imaging of Antibodies to Canine Cardiac Myosin with Indium–111–Diethylenetriamine Pentaacetic Acid," *Science* 209:295–297, American Association for the Advancement of Science (1980).

Kishimoto, T.K., et al., "Cloning of the α subunit of LFA–1, Mac–1, and p150,95: Homology to a fibronectin receptor and the molecular basis of leukocyte adhesion deficiency," *Fed. Proc.* 46:Abstract 755, Federation of American Societies for Experimental Biology (Mar. 1987).

Kishimoto, T.K., et al., "The α Subunit of LFA–1, Mac–1, and p150,95: Gene Cloning, Homology to a Fibronectin Receptor, and the Molecular Basis of Leukocyte Adhesion Deficiency," *J. Cell Biochem.* (*Supplement 11D*): Abstract T415, Wiley–Liss (Mar. 1987).

Kogan, T.P., et al., "A Single Amino Acid Residue Can Determine the Ligand Specificity of E–selectin," *J. Biol. Chem.* 270:14047–14055, American Society for Biochemistry and Molecular Biology (1995).

Kohl, S., et al., "The Genetic Deficiency of Leukocyte Surface Glycoprotein Mac–1, LFA–1, p150,95 in Humans is Associated with Defective Antibody–Dependent Cellular Cytotoxicity In Vitro and Defective Protection Against Herpes Simplex Virus Infection In Vivo," *J. Immunol.* 137:1688–1694, American Association of Immunologists (1986).

Krensky, A.M., et al., "LFA–1, LFA–2, and LFA–3 Antigens Are Involved in CTL–Target Conjugation," *J. Immunol.* 132:2180–2182, American Association of Immunologists (1984).

Lanier, L.L., et al., "p150/95, Third Member of the LFA–1/ CR₃ polypeptide family identified by anti–Leu M5 monoclonal antibody," *Eur. J. Immunol.* 15:713–718, Verlag (1985).

Lathe, R., "Synthetic Oligonucleotide Probes Deduced from Amino Acid Sequence Data. Theoretical and Practical Considerations," *J. Mol. Biol.* 183:1–12, Academic Press, Inc. (1985).

Makgoba, M.W., et al., "ICAM–1 a ligand for LFA–1–dependent adhesion of B, T and myeloid cells," *Nature* 331:86–88, Macmillan Journals Ltd. (Jan. 1988).

Marlin, S.D., and Springer, T.A., "Purified Intercellular Adhesion Molecule–1 (ICAM–1) is a Ligand for Lymphocyte Function–Associated Antigen 1 (LFA–1)," *Cell* 51:813–819, Cell Press (Dec. 1987).

Martz, E., "Immune T Lymphocyte to Tumor Cell Adhesion. Magnesium Sufficient, Calcium Insufficient," *J. Cell Biol.* 84:584–598, Rockefeller University Press (1980).

Micklem, K.J., and Sim, R.B., "Isolation of complement–fragment–iC3b–binding proteins by affinity chromatography. The identification of p150,95 as an iC3b–binding protein," *Biochem. J.* 231:233–236, Portland Press (1985).

Miller, L.J., et al., "Regulated Expression of the Mac–1, LFA–1, p150,95 Glycoprotein Family During Leukocyte Differentiation," *J. Immunol.* 137:2891–2900, American Association of Immunologists (1986).

Miller, L.J., et al., "Purification and α Subunit N–terminal Sequences of Human Mac–1 and p150,95 Leukocyte Adhesion Proteins," *J. Immunol.* 138:2381–2383, American Association of Immunologists (Apr. 1987).

Mosser, D.M., and Edelson, P.J., "The Mouse Macrophage Receptor for C3bi (CR3) is a Major Mechanism in the Phagocytosis of *Leishmania Promastigotes,*" *J. Immunol.* 135:2785–2789, American Association of Immunologists (1985).

Pattaroyo, M., et al., "Identification of a Cell–Surface Glycoprotein Mediating Cell Adhesion in EBV–Immortalized Normal B Cells," *Int. J. Cancer* 38:539–547, Wiley–Liss (1986).

Patarroyo, M., et al., "Identification of a novel adhesion molecule in human leukocytes by monoclonal antibody LB–2," *FEBS Lett.* 210:127–131, Elsevier Science (Jan. 1987).

Patarroyo, M., et al., "Adhesion–Mediating Molecules of Human Monocytes," *Cell. Immunol.* 113:278–289, Academic Press (May 1988).

Pierce, M.W., et al., "N–terminal sequence of human leukocyte glycoprotein Mo1: conservation across species and homology to platelet IIb/IIIa," *Biochim. Biophys. Acta* 874:368–371, Elsevier Publishing Co. (1986).

Pober, J.S., et al., "Overlapping Patterns of Activation of Human Endothelial Cells by Interleukin 1, Tumor Necrosis Factor, and Immune Interferon," *J. Immunol.* 137:1893–1896, American Association of Immunologists (1986).

Pohlman, T.H., t al., "An Endothelial Cell Surface Factor(s) Induced In Vitro by Lipopolysaccharide, Interleukin 1, and Tumor Necrosis Factor–α Increases Neutrophil Adherence by a CDw18–Dependent Mechanism," *J. Immunol.* 136:4548–4553, American Association of Immunologists (1986).

Poltorak, M., et al., "Myelin–associated Glycoprotein, a Member of the L2/HNK–1 Family of Neural Cell Adhesion Molecules, Is Involved in Neuron–Oligodendrocyte and Oligodendrocyte—Oligodendrocyte Interaction," *J. Cell Biol.* 105:1893–1899, Rockefeller University Press (Oct. 1987).

Prieto, J., et al., "Molecules mediating adhesion and T and B cells, monocytes and granulocytes to vascular endothelial cells," *Immunology* 63:631–637, Blackwell Scientific Publications (Apr. 1988).

Pytela, R., "Amino acid sequence of the murine Mac–1 α chain reveals homology with the integrin family and an additional domain related to von Willebrand factor," *EMBO J.* 7:1371–1378, Oxford University Press (May 1988).

Rothlein, R., and Springer, T.A., "The Requirement for Lymphocyte Function–Associated Antigen 1 in Homotypic Leukocyte Adhesion Stimulated by Phorbol Ester," *J. Exp. Med.* 163:1132–1149, Rockefeller University Press (1986).

Rothlein, R., et al., "A Human Intercellular Adhesion Molecule (ICAM–1) Distinct From LFA–1," *J. Immunol.* 137:1270–1274, American Association of Immunologists (1986).

Ruoslahti, E., and Pierschbacher, M.D., "New Perspectives in Cell Adhesion: RGD and Integrins," *Science* 238:491–497, American Association for the Advancement of Science (Oct. 1987).

Salzer, J.L., et al., "The Amino Acid Sequences of the Myelin–associated Glycoproteins: Homology to the Immunoglobulin Gene Superfamily," *J. Cell Biol.* 104:957–965, Rockefeller University Press (Apr. 1987).

Sambrook, J., et al., in *Molecular Cloning: A Laboratory Manual,* Cold Spring Harbor Laboratory Press, New York (1982), p. 5.

Sanchez–Madrid, F., et al., "Mapping of Antigenic and Functional Epitopes on the α– and β–subunits of Two Related Mouse Glycoproteins Involved in Cell Interactions, LFA–1 and Mac–1," *J. Exp. Med.* 158:586–602, Rockefeller University Press (1983).

Sanchez–Madrid, F., et al., "A Human Leukocyte Differentiation Antigen Family with Distinct α–subunits and a Common β–Subunit: The Lymphocyte Function–Associated Antigen (LFA–1), the C3bi complement receptor (OKM1–Mac1), and the p150,95 molecule," *J. Exp. Med.* 158:1785–1803, Rockefeller University Press (1983).

Sastre, L., et al., "A partial genomic DNA clone for the α subunit of the mouse complement receptor type 3 and cellular adhesion molecule Mac–1," *Proc. Natl. Acad. Sci. USA* 83:5644–48, National Academy of Sciences (1986).

Schwarting, R., et al., "The Monoclonal Antibodies αS–HCL 1 (αLeu–14) and αS–HCL 3 (αLeu–M5) Allow the Diagnosis of Hairy Cell Leukemia," *Blood* 65:974–983, American Society of Hematology (1985).

Seed, B., and Aruffo, A., "Molecular cloning of the Cd2 antigen, the T–cell erythrocyte receptor, by a rapid immunoselection procedure," *Proc. Natl. Acad. Sci. USA* 84:3365–3369, National Academy of Science (May 1987).

Simpson, P.J., et al., "Reduction of Experimental Canine Myocardial Reperfusion Injury by a Monoclonal Antibody (Anti–Mo1, Anti–CD11b) That Inhibits Leukocyte Adhesion," *J. Clin. Invest.* 81:624–629, American Society for Clinical Investigation (Feb. 1988).

Smith, C.W., et al., "Motility and Adhesiveness in Human Neutrophils. Effects of Chemotactic Factors," *J. Clin. Invest.* 63:221–229, American Society for Clinical Investigation (1979).

Springer, T., et al., "MAC–1: a macrophage differentiation antigen identified by monoclonal antibody," *Eur. J. Immunol.* 9:301–306, Verlag (1979).

Springer, T.A., et al., "LFA–1 and Lyt–2,3, Molecules Associated with T Lymphocyte–Mediating Killing; and Mac–1, and LFA–1 Homologue Associated with Complement Receptor Function," *Immunol. Rev.* 68:171–195, Munksgaard International Publishers (1982).

Springer, T.A., et al., "Inherited Deficiency of the Mac–1, LFA–1, p150,95 Glycoprotein Family and its Molecular Basis," *J. Exp. Med. 160*:1901–1918, Rockefeller University Press (1984).

Springer, T.A., et al., "The Lymphocyte Function–Associated LFA–1, CD2, and LFA–3 Molecules: Cell Adhesion Receptors of the Immune System," *Ann. Rev. Immunol. 5*:223–252, Annual Reviews Inc. (Apr. 1987).

Strassman, G., et al., "Mechanisms of Tumor Cell Capture by Activated Macrophages: Evidence for Involvement of Lymphocyte Function–Associated (LFA)–1 Antigen," *J. Immunol. 136*:4328–4333, American Association of Immunologists (1986).

Todd, R.F., et al., "Subcellular Localization of the Large Subunit of Mo1 (Mo1$_\alpha$; formerly gp110), a Surface Glycoprotein Associated with Neutrophil Adhesion," *J. Clin. Invest. 74*:1280–1290, American Society for Clinical Investigation (1984).

Todd, R.F., and Freyer, D.R., "CD11/CD18 Leukocyte Glycoprotein Deficiency," *Hematol. Oncol. Clin. North Am. 2*:13–31, W.B. Saunders (Mar. 1988).

Unger, E.C., et al., "Magnetic Resonance Imaging Using Gadolinium Labeled Monoclonal Antibody," *Invest. Radiol. 7*:693–700, Lippincott Williams & Wilkins (1985).

Vedder, N.B., and Harlan, J.M., "Increased Surface Expression of CD11b/CD18 (Mac–1) Is Not Required for Stimulated Neutrophil Adherence to Cultured Endothelium," *J. Clin. Invest. 81*:676–682, American Society for Clinical Investigation (Mar. 1988).

Wallis, W.J., et al., "Human Monocyte Adherence to Cultured Vascular Endothelium: Monoclonal Antibody–Defined Mechanisms," *J. Immunol. 135*:2323–2330, American Association of Immunologists (1985).

Ward, P.A., and Mulligan, M.S., "Blocking of adhesion molecules in vivo as anti–inflammatory therapy," *Ther. Immunol. 1*:165–171, Blackwell Scientific Publications (1994).

Yancey, K.B., et al., "Human C5a Modulates Monocyte to Fc and C3 Receptor Expression," *J. Immunol. 135*:465–470, American Association of Immunologists (1985).

\* cited by examiner

```
                                GAATTCCGTGGTTCCTCAGTGGTGCCTGCAACCCCTGGTTCACCTCCTTCCAGGTTC

TGGCTCCTTCCAGCC ATG GCT CTC AGA GTC CTT CTG TTA ACA GCC TTG ACC TTA TGT CAT GGG   120
                Met Ala Leu Arg Val Leu Leu Leu Thr Ala Leu Thr Leu Cys His Gly    -1

TTC AAC TTG GAC ACT GAA AAC GCA ATG ACC TTC CAA GAG AAC GCA AGG GGC TTC GGG CAG
Phe Asn Leu Asp Thr Glu Asn Ala Met Thr Phe Gln Glu Asn Ala Arg Gly Phe Gly Gln

AGC GTG GTC CAG CTT CAG GGA TCC AGG GTG GTG GTT GGA GCC CCC CAG GAG ATA GTG GCT   240
Ser Val Val Gln Leu Gln Gly Ser Arg Val Val Val Gly Ala Pro Gln Glu Ile Val Ala    40

GCC AAC CAA AGG GGC AGC CTC TAC CAG TGC GAC TAC AGC ACA GGC TCA TGC GAG CCC ATC
Ala Asn Gln Arg Gly Ser Leu Tyr Gln Cys Asp Tyr Ser Thr Gly Ser Cys Glu Pro Ile

CGC CTG CAG GTC CCG GTG GAG GCC GTG AAC ATG TCC CTG GGC CTG TCC CTG GCA GCC ACC   360
Arg Leu Gln Val Pro Val Glu Ala Val Asn Met Ser Leu Gly Leu Ser Leu Ala Ala Thr    80

ACC AGC CCC CCT CAG CTG CTG GCC TGT GGT CCC ACC GTG CAC CAG ACT TGC AGT GAG AAC
Thr Ser Pro Pro Gln Leu Leu Ala Cys Gly Pro Thr Val His Gln Thr Cys Ser Glu Asn

ACG TAT GTG AAA GGG CTC TGC TTC CTG TTT GGA TCC AAC CTA CGG CAG CAG CCC CAG AAG   480
Thr Tyr Val Lys Gly Leu Cys Phe Leu Phe Gly Ser Asn Leu Arg Gln Gln Pro Gln Lys   120

TTC CCA GAG GCC CTC CGA GGG TGT CCT CAA GAG GAT AGT GAC ATT GCC TTC TTG ATT GAT
Phe Pro Glu Ala Leu Arg Gly Cys Pro Gln Glu Asp Ser Asp Ile Ala Phe Leu Ile Asp
```

FIG.2A

```
GGC TCT GGT AGC ATC ATC CCA CAT GAC TTT CGG CGG ATG AAG GAG TTT GTC TCA ACT GTG   600
Gly Ser Gly Ser Ile Ile Pro His Asp Phe Arg Arg Met Lys Glu Phe Val Ser Thr Val   160

ATG GAG CAA TTA AAA AAG TCC AAA ACC TTG TTC TCT TTG ATG CAG TAC TCT GAA GAA TTC
Met Glu Gln Leu Lys Lys Ser Lys Thr Leu Phe Ser Leu Met Gln Tyr Ser Glu Glu Phe

CGG ATT CAC TTT ACC TTC AAA GAG TTC CAG AAC AAC CCT AAC CCA AGA TCA CTG GTG AAG   720
Arg Ile His Phe Thr Phe Lys Glu Phe Gln Asn Asn Pro Asn Pro Arg Ser Leu Val Lys   200

CCA ATA ACG CAG CTG CTT GGG CGG ACA CAC ACG GCC ACG GGC ATC CGC AAA GTG GTA CGA
Pro Ile Thr Gln Leu Leu Gly Arg Thr His Thr Ala Thr Gly Ile Arg Lys Val Val Arg

GAG CTG TTT AAC ATC ACC AAC GGA GCC CGA AAG AAT GCC TTT AAG ATC CTA GTT GTC ATC   840
Glu Leu Phe Asn Ile Thr Asn Gly Ala Arg Lys Asn Ala Phe Lys Ile Leu Val Val Ile   240

ACG GAT GGA GAA AAG TTT GGC GAT CCC TTG GGA TAT GAG GAT GTC ATC CCT GAG GCA GAC
Thr Asp Gly Glu Lys Phe Gly Asp Pro Leu Gly Tyr Glu Asp Val Ile Pro Glu Ala Asp

AGA GAG GGA GTC ATT CGC TAC GTC ATT GGG GTG GGA GAT GCC TTC CGC AGT GAG AAA TCC   960
Arg Glu Gly Val Ile Arg Tyr Val Ile Gly Val Gly Asp Ala Phe Arg Ser Glu Lys Ser   280

CGC CAA GAG CTT AAT ACC ATC GCA TCC AAG CCG CCT CGT GAT CAC GTG TTC CAG GTG AAT
Arg Gln Glu Leu Asn Thr Ile Ala Ser Lys Pro Pro Arg Asp His Val Phe Gln Val Asn

AAC TTT GAG GCT CTG AAG ACC ATT CAG AAC CAG CTT CGG GAG AAG ATC TTT GCG ATC GAG  1080
Asn Phe Glu Ala Leu Lys Thr Ile Gln Asn Gln Leu Arg Glu Lys Ile Phe Ala Ile Glu   320
```

FIG.2B

```
GGT ACT CAG ACA GGA AGT AGC AGC TCC TTT GAG CAT GAG ATG TCT CAG GAA GGC TTC AGC
Gly Thr Gln Thr Gly Ser Ser Ser Ser Phe Glu His Glu Met Ser Gln Glu Gly Phe Ser

GCT GCC ATC ACC TCT AAT GGC CCC TTG CTG AGC ACT GTG GGG AGC TAT GAC TGG GCT GGT 1200
Ala Ala Ile Thr Ser Asn Gly Pro Leu Leu Ser Thr Val Gly Ser Tyr Asp Trp Ala Gly  360

GGA GTC TTT CTA TAT ACA TCA AAG GAG AAA AGC ACC TTC ATC AAC ATG ACC AGA GTG GAT
Gly Val Phe Leu Tyr Thr Ser Lys Glu Lys Ser Thr Phe Ile Asn Met Thr Arg Val Asp

TCA GAC ATG AAT GAT GCT TAC TTG GGT TAT GCT GCC GCC ATC ATC TTA CGG AAC CGG GTG 1320
Ser Asp Met Asn Asp Ala Tyr Leu Gly Tyr Ala Ala Ala Ile Ile Leu Arg Asn Arg Val  400

CAA AGC CTG GTT CTG GGG GCA CCT CGA TAT CAG CAC ATC GGC CTG GTA GCG ATG TTC AGG
Gln Ser Leu Val Leu Gly Ala Pro Arg Tyr Gln His Ile Gly Leu Val Ala Met Phe Arg

CAG AAC ACT GGC ATG TGG GAG TCC AAC GCT AAT GTC AAG GGC ACC CAG ATC GGC GCC TAC 1440
Gln Asn Thr Gly Met Trp Glu Ser Asn Ala Asn Val Lys Gly Thr Gln Ile Gly Ala Tyr  440

TTC GGG GCC TCC CTC TGC TCC GTG GAC GTG GAC AGC AAC GGC AGC ACC GAC CTG GTC CTC
Phe Gly Ala Ser Leu Cys Ser Val Asp Val Asp Ser Asn Gly Ser Thr Asp Leu Val Leu

ATC GGG GCC CCC CAT TAC TAC GAG CAG ACC CGA GGG GGC CAG GTG TCC GTG TGC CCC TTG 1560
Ile Gly Ala Pro His Tyr Tyr Glu Gln Thr Arg Gly Gly Gln Val Ser Val Cys Pro Leu  480

CCC AGG GGG CAG AGG GCT CGG TGG CAG TGT GAT GCT GTT CTC TAC GGG GAG CAG GGC CAA
Pro Arg Gly Gln Arg Ala Arg Trp Gln Cys Asp Ala Val Leu Tyr Gly Glu Gln Gly Gln
```

FIG.2C

```
CCC TGG GGC CGC TTT GGG GCA GCC CTA ACA GTG CTG GGG GAC GTA AAT GGG GAC AAG CTG 1680
Pro Trp Gly Arg Phe Gly Ala Ala Leu Thr Val Leu Gly Asp Val Asn Gly Asp Lys Leu  520

ACG GAC GTG GCC ATT GGG GCC CCA GGA GAG GAG GAC AAC CGG GGT GCT GTT TAC CTG TTT
Thr Asp Val Ala Ile Gly Ala Pro Gly Glu Glu Asp Asn Arg Gly Ala Val Tyr Leu Phe

CAC GGA ACC TCA GGA TCT GGC ATC AGC CCC TCC CAT AGC CAG CGG ATA GCA GGC TCC AAG 1800
His Gly Thr Ser Gly Ser Gly Ile Ser Pro Ser His Ser Gln Arg Ile Ala Gly Ser Lys  560

CTC TCT CCC AGG CTC CAG TAT TTT GGT CAG TCA CTG AGT GGG GGC CAG GAC CTC ACA ATG
Leu Ser Pro Arg Leu Gln Tyr Phe Gly Gln Ser Leu Ser Gly Gly Gln Asp Leu Thr Met

GAT GGA CTG GTA GAC CTG ACT GTA GGA GCC CAG GGG CAC GTG CTG CTC CTC AGG TCC CAG 1920
Asp Gly Leu Val Asp Leu Thr Val Gly Ala Gln Gly His Val Leu Leu Leu Arg Ser Gln  600

CCA GTA CTG AGA GTC AAG GCA ATC ATG GAG TTC AAT CCC AGG GAA GTG GCA AGG AAT GTA
Pro Val Leu Arg Val Lys Ala Ile Met Glu Phe Asn Pro Arg Glu Val Ala Arg Asn Val

TTT GAG TGT AAT GAT CAG GTG GTG AAA GGC AAG GAA GCC GGA GAG GTC AGA GTC TGC CTC 2040
Phe Glu Cys Asn Asp Gln Val Val Lys Gly Lys Glu Ala Gly Glu Val Arg Val Cys Leu  640

CAT GTC CAG AAG AGC ACA CGG GAT CGG CTA AGA GAA GGA CAG ATC CAG AGT GTT GTG ACT
His Val Gln Lys Ser Thr Arg Asp Arg Leu Arg Glu Gly Gln Ile Gln Ser Val Val Thr

TAT GAC CTG GCT CTG GAC TCC GGC CGC CCA CAT TCC CGC GCC GTC TTC AAT GAG ACA AAG 2160
Tyr Asp Leu Ala Leu Asp Ser Gly Arg Pro His Ser Arg Ala Val Phe Asn Glu Thr Lys  680
```

FIG.2D

```
AAC AGC ACA CGC AGA CAG ACA CAG GTC TTG GGG CTG ACC CAG ACT TGT GAG ACC CTG AAA
Asn Ser Thr Arg Arg Gln Thr Gln Val Leu Gly Leu Thr Gln Thr Cys Glu Thr Leu Lys

CTA CAG TTG CCG AAT TGC ATC GAG GAC CCA GTG AGC CCC ATT GTG CTG CGC CTG AAC TTC  2280
Leu Gln Leu Pro Asn Cys Ile Glu Asp Pro Val Ser Pro Ile Val Leu Arg Leu Asn Phe   720

TCT CTG GTG GGA ACG CCA TTG TCT GCT TTC GGG AAC CTC CGG CCA GTG CTG GCG GAG GAT
Ser Leu Val Gly Thr Pro Leu Ser Ala Phe Gly Asn Leu Arg Pro Val Leu Ala Glu Asp

GCT CAG AGA CTC TTC ACA GCC TTG TTT CCC TTT GAG AAG AAT TGT GGC AAT GAC AAC ATC  2400
Ala Gln Arg Leu Phe Thr Ala Leu Phe Pro Phe Glu Lys Asn Cys Gly Asn Asp Asn Ile   760

TGC CAG GAT GAC CTC AGC ATC ACC TTC AGT TTC ATG AGC CTG GAC TGC CTC GTG GTG GGT
Cys Gln Asp Asp Leu Ser Ile Thr Phe Ser Phe Met Ser Leu Asp Cys Leu Val Val Gly

GGG CCC CGG GAG TTC AAC GTG ACA GTG ACT GTG AGA AAT GAT GGT GAG GAC TCC TAC AGG  2520
Gly Pro Arg Glu Phe Asn Val Thr Val Thr Val Arg Asn Asp Gly Glu Asp Ser Tyr Arg   800

ACA CAG GTC ACC TTC TTC TTC CCG CTT GAC CTG TCC TAC CGG AAG GTG TCC ACA CTC CAG
Thr Gln Val Thr Phe Phe Phe Pro Leu Asp Leu Ser Tyr Arg Lys Val Ser Thr Leu Gln

AAC CAG CGC TCA CAG CGA TCC TGG CGC CTG GCC TGT GAG TCT GCC TCC TCC ACC GAA GTG  2640
Asn Gln Arg Ser Gln Arg Ser Trp Arg Leu Ala Cys Glu Ser Ala Ser Ser Thr Glu Val   840

TCT GGG GCC TTG AAG AGC ACC AGC TGC AGC ATA AAC CAC CCC ATC TTC CCG GAA AAC TCA
Ser Gly Ala Leu Lys Ser Thr Ser Cys Ser Ile Asn His Pro Ile Phe Pro Glu Asn Ser
```

FIG.2E

```
GAG GTC ACC TTT AAT ATC ACG TTT GAT GTA GAC TCT AAG GCT TCC CTT GGA AAC AAA CTG 2760
Glu Val Thr Phe Asn Ile Thr Phe Asp Val Asp Ser Lys Ala Ser Leu Gly Asn Lys Leu  880

CTC CTC AAG GCC AAT GTG ACC AGT GAG AAC AAC ATG CCC AGA ACC AAC AAA ACC GAA TTC
Leu Leu Lys Ala Asn Val Thr Ser Glu Asn Asn Met Pro Arg Thr Asn Lys Thr Glu Phe

CAA CTG GAG CTG CCG GTG AAA TAT GCT GTC TAC ATG GTG GTC ACC AGC CAT GGG GTC TCC 2880
Gln Leu Glu Leu Pro Val Lys Tyr Ala Val Tyr Met Val Val Thr Ser His Gly Val Ser  920

ACT AAA TAT CTC AAC TTC ACG GCC TCA GAG AAT ACC AGT CGG GTC ATG CAG CAT CAA TAT
Thr Lys Tyr Leu Asn Phe Thr Ala Ser Glu Asn Thr Ser Arg Val Met Gln His Gln Tyr

CAG GTC AGC AAC CTG GGG CAG AGG AGC CTC CCC ATC AGC CTG GTG TTC TTG GTG CCC GTC 3000
Gln Val Ser Asn Leu Gly Gln Arg Ser Leu Pro Ile Ser Leu Val Phe Leu Val Pro Val  960

CGG CTG AAC CAG ACT GTC ATA TGG GAC CGC CCC CAG GTC ACC TTC TCC GAG AAC CTC TCG
Arg Leu Asn Gln Thr Val Ile Trp Asp Arg Pro Gln Val Thr Phe Ser Glu Asn Leu Ser

AGT ACG TGC CAC ACC AAG GAG CGC TTG CCC TCT CAC TCC GAC TTT CTG GCT GAG CTT CGG 3120
Ser Thr Cys His Thr Lys Glu Arg Leu Pro Ser His Ser Asp Phe Leu Ala Glu Leu Arg 1000

AAG GCC CCC GTG GTG AAC TGC TCC ATC GCT GTC TGC CAG AGA ATC CAG TGT GAC ATC CCG
Lys Ala Pro Val Val Asn Cys Ser Ile Ala Val Cys Gln Arg Ile Gln Cys Asp Ile Pro

TTC TTT GGC ATC CAG GAA GAA TTC AAT GCT ACC CTC AAA GGC AAC CTC TCG TTT GAC TGG 3240
Phe Phe Gly Ile Gln Glu Glu Phe Asn Ala Thr Leu Lys Gly Asn Leu Ser Phe Asp Trp 1040
```

FIG.2F

```
TAC ATC AAG ACC TCG CAT AAC CAC CTC CTG ATC GTG AGC ACA GCT GAG ATC TTG TTT AAC
Tyr Ile Lys Thr Ser His Asn His Leu Leu Ile Val Ser Thr Ala Glu Ile Leu Phe Asn

GAT TCC GTG TTC ACC CTG CTG CCG GGA CAG GGG GCG TTT GTG AGG TCC CAG ACG GAG ACC   3360
Asp Ser Val Phe Thr Leu Leu Pro Gly Gln Gly Ala Phe Val Arg Ser Gln Thr Glu Thr   1080

AAA GTG GAG CCG TTC GAG GTC CCC AAC CCC CTG CCG CTC ATC GTG GGC AGC TCT GTC GGG
Lys Val Glu Pro Phe Glu Val Pro Asn Pro Leu Pro Leu Ile Val Gly Ser Ser Val Gly

GGA CTG CTG CTC CTG GCC CTC ATC ACC GCC GCG CTG TAC AAG CTC GGC TTC TTC AAG CGG   3480
Gly Leu Leu Leu Leu Ala Leu Ile Thr Ala Ala Leu Tyr Lys Leu Gly Phe Phe Lys Arg   1120

CAA TAC AAG GAC ATG ATG AGT GAA GGG GGT CCC CCG GGG GCC GAA CCC CAG TAG CGGCTCC
Gln Tyr Lys Asp Met Met Ser Glu Gly Gly Pro Pro Gly Ala Glu Pro Gln  *

TTCCCGACAGAGCTGCCTCTCGGTGGCCAGCAGGACTCTGCCCAGACCACACGTAGCCCCCAGGCTGCTGGACACGTCGG  3621
                                                                                 1137
 ↓
ACAGCGAAGTATCCCCGACAGGACGGGCTTGGGCTTCCATTTGTGTGTGTGCAAGTGTGTATGTGCGTGTGTGCGAGTGT

GTGCAAGTGTCTGTGTGCAAGTGTGTGCACGTGTGCGTGTGCGTGCATGTGCACTCGCACGCCCATGTGTGAGTGTGTG  3780

CAAGTATGTGAGTGTGTCCAGTGTGTGTGCGTGTGTCCATGTGTGTGCAGTGTGTGCATGTGTGCGAGTGTGTGCATGTG

TGTGCTCAGGGGCTGTGGCTCACGTGTGTGACTCAGAGTGTCTCTGGCGTGTGGGTAGGTGACGGCAGCGTAGCCTCTC  3939

CGGCAGAAGGGAACTGCCTGGGCTCCCTTGTGCGTGGGTAAGCCGCTGCTGGGTTTTCCTCCGGGAGAGGGGACGGTCAA
```

FIG.2G

TCCTGTGGGTGAAGAGAGAGGGAAACACAGCAGCATCTCTCCACTGAAAGAAGTGGGACTTCCCGTCGCCTGCGAGCCT 4098

GCGGCCTGCTGGAGCCTGCGCAGCTTGGATGGATACTCCATGAGAAAAGCCGTGGGTGGAACCAGGAGCCTCCTCCACAC

CAGCGCTGATGCCCAATAAAGATGCCCACTGAGGAATCATGAAGCTTCCTTTCTGGATTCATTTATTATTTCAATGTGA 4257

CTTTAATTTTTTGGATGGATAAGCCTGTCTATGGTACAAAAATCACAAGGCATTCAAGTGTACAGTGAAAAGTCTCCCTT

TCCAGATATTCAAGTCACCTCCTTAAAGGTAGTCAAGATTGTGTTTTGAGGTTTCCTTCAGACAGATTCCAGGCGATGT 4416

GCAAGTGTATGCACGTGTGCACACACCACACACATACACACACACAAGCTTTTTTACACAAATGGTAGCATACTTTATAT

TGGTCTGTATCTTGCTTTTTTTTCACCAATATTTCTCAGACATCGGTTCATATTAAGACATAAATTACTTTTTCATTCTT 4575

TTATACCGCTGCATAGTATTCCATTGTGTGAGTGTACCATAATGTATTTAACCAGTCTTCTTTTGATATACTATTTTCAT

TCTCTTGTTATTGCATCAATGCTGAGTTAATAAATCAAATATATGTCAAAAAAAAAAAAAAAA.....AAAAAAAAAA 4740

FIG.2H

```
   I     4 DTENAMTFQENARGFGQSVVQLQGSR-----VVGAPQEIVAAN QRGSLYQCDYSTGSCE          58
  II    59 PIRLQVPVELAVNMSLGLSLAATTSPPQ-LIACGPTVHQTCS-ENTYVVKGLCFLFG              111
 III   326 SSSSF-EHEMSQEFSAAII---SNGPLLS--TVGS-Y---DWAGG---IVFLIY--TSKEKSTF        373
  IV   374 INMTRVDSDMNDAYLGYAA-AIILRNRVQS--IVL-GAPRY--QHIGLVAMFRQN--TGMW          426
   V   427 ESNANVKGTQIGAYFGASL-CSVDVDSNGSTDLVLIGAPHYY-EQIRGGQVSVCPLPRGQRARWQCD    491
  VI   492 AVLYGEQGQPWGR-FGAALTVLGDVNGDKLTD-VAIGAPGE--EDNRG-AVYLFHGTSGSGISPSHS    553
 VII   554 QRIAGSKLSPRLQYFGQSLSGGQDTMDGLVDLI-TVGAQGHV-LLLRIS-QPVLRVKATMEFNPREVA   617

DIV. CATION-BINDING CONSENSUS SEQUENCE      D--DGDG-ID--E

DIV. CATION-COORDINATING RESIDUES           +X +Y +Z -Y -X   -Z
FLANKING CONSENSUS
SEQ. (Mac-1)                                YFGASL------------LVTVGAP
                                                 A
FLANKING CONSENSUS
SEQ. (Integrins)                            SYFG-SV-----------LVVGAP
```

```
           ELFNITNGARKNAFKILVITDGEKFGDPLGYEDVIPEADREGVIRYVIGVGDAFRSEKSRQEL
Mac-1
p150,95    RLFHASYGARRDATKILILIVITDGKKEGDSLDYKDVIPMADAAGIIRYAIGVGLAFQNRNSVWKEL
IIb        ----------------------------------------------------------------
VNR        ----------------------------------------------------------------
FNR        ----------------------------------------------------------------

347
                                                                   345
                                                                   180
                                                                   168
                                                                   177
           NTIASKPPRDHVFQVNNFEALKTIQNQLREKIFAIEGTQTGSSSFEHEMSQEGFSAAITSNG-
Mac-1
p150,95    NDIASKPSQEHIFKVEDFDALKDIQNQLKEKIFAIEGTETTSSSFELEMAQEGFSAVFTPDG-
IIb        --------------------------------GFSSVVTQAGE
VNR        --------------------------------GFSIDFTKADR
FNR        -------------------------------GFSAEFIKTGR
```

```
Mac-1    SFDWYIKTSHNHLLIVST---AEILFNDSV---FTLLPGQGAFVRSQTETKVEPFEVPN--PLPL        1137
p150,95  SFFGWVRQILQKKVSVSV---AEITFDTSV--YSQLPGQEAFMRAQTTTVLEKYKVHN--PTPL        1144
IIb      AFLWLPSLYQR--PLDQFVLQSHAWFNVSSLPYAVPPLSLPRGEAQVTQLLRALEERAIPIVN         1008
VNR      SLLWTETFMNKENQNHSYSLKSSASENVIEFPYKNLPIEDIINSTLVTTNVTWGIQPAPMPVPV        1018
FNR      FRVWAKTFLQREHQPFS--LQCEAVYKALKMPYRILPQKERQVATAVQVTKAEGSYGVPL           1017

IVGSSV---GGLLLLALITAALYKLGFFKRQ--YKDMMSEGGPPGAEPQ--ENGTQTPSPPSEK
         IVGSSI---GGLLLLALITAVLYKVGFFKRQ--YKEMMEEANGQIAP--EEDDEEGE
         VLV--GVLGGLLLLTILVLAMWKVGFFKRNRPPL---EEQEREQLQPHENGEGNSET
         WIIILAVLAGLLLLAVLVFVMYRMGFFKRVRPPQ--EEEQEREQLQPHENGEGNSET
         WIIILAILFGLLLLGLIYILYKLGFFKRSLPYGTAMEKAQLK-PPATSBA
                    TM

ALPHA-SUBUNIT OF THE MAC-1 LEUKOCYTE ADHESION RECEPTOR

CROSS-REFERENCE TO RELATED APPLICATIONS

This application is a continuation of U.S. appl. Ser. No. 08/979,940, filed Nov. 26, 1997, now abandoned; which is a divisional of U.S. appl. Ser. No. 08/433,801, filed May 3, 1995, now U.S. Pat. No. 5,849,896, issued Dec. 15, 1998; which is a continuation of U.S. appl. Ser. No. 08/077,098, filed Jun. 16, 1993, now abandoned; which is a continuation of U.S. appl. Ser. No. 07/942,056, filed Sep. 8, 1992, now abandoned; which is a continuation of U.S. appl. Ser. No. 07/321,239, filed Mar. 9, 1989, now abandoned; which is a continuation-in-part of U.S. appl. Ser. No. 07/235,353, filed Aug. 23, 1988, now abandoned.

FIELD OF THE INVENTION

The present invention relates to the leukocyte adhesion receptor Mac-1. The invention further pertains to the cloning of DNA sequences which encode the alpha-subunit of this molecule. This invention was made in part with government support. The government has certain rights in this invention.

DESCRIPTION OF THE RELATED ART

The immune system is responsible for protecting an animal from foreign invaders, such as bacteria, viruses, etc. An excellent review of the defense system is provided by Eisen, H. W. (In: *Microbiology*, 3rd Ed., Harper & Row, Philadelphia, Pa. (1980), pp. 290–295 and 381–418). The ability of the immune system to protect an animal against foreign invaders depends, in large measure, on the presence and function of blood cells known an leukocytes. The ability of leukocytes to provide such protection has been found to require that these cells adhere to cellular and extracellular substrates.

For example, leukocytes must be able to attach to endothelial cells so that they can migrate from circulation to sites of ongoing inflammation. Furthermore, they must attach to antigen-presenting cells so that a normal immune response can occur. They must also be able to attach to appropriate target cells so that the lysis of virally-infected (or tumor) cells can occur. Furthermore, leukocytes must be able to attach to various activated proteins (such as iC3b-the activated form of the third component of complement) so that they may efficiently phagocytose and clear microbial and cellular debris. Thus, leukocyte adhesion is a requisite of a normally functioning host defense system. The inhibition of this defense system is desirable in cases such as transplantation, because the host "sees" the transplanted tissue as foreign and initiates an immune response to that tissue. Leukocyte adhesion is, therefore, also involved in the rejection of transplanted tissue and organs. Thus, an understanding of leukocyte adhesion may enable one to either augment an animal's ability to fight infection or suppress an animal's capacity to reject transplanted tissue.

Recently, leukocyte surface molecules involved in mediating leukocyte adhesion were identified using hybridoma technology. Briefly, monoclonal antibodies directed against human T-cells (Davignon, D., et al., *Proc. Natl. Acad. Sci. USA* 78:4535–4539 (1981)) and mouse spleen cells (Springer, T., et al., *Eur. J. Immunol.* 9:301–306 (1979)) were identified which bound to leukocyte surfaces and inhibited the attachment-related functions described above (Springer, T., et al., *Fed. Proc.* 44:2660–2663 (1985)). The molecules which were recognized by these antibodies comprise a set of leukocyte adhesion receptors known as the "Lymphocyte Function-Associated Antigen-1 family" (or the "LFA-1 family") of adhesion receptor molecules.

The LFA-1 family of adhesion receptor molecules contains three highly related cell surface glycoproteins. These glycoproteins have been found to mediate cell-cell interactions in inflammation. The glycoproteins have been designated "LFA-1" (lymphocyte function-associated antigen-1), "Mac-1" and "p150,95." Whereas LFA-1 is found on the surfaces of most leukocytes (Springer, T. A., et al., *Immunol. Rev.* 68:111–135 (1982)), Mac-1 and p150,95 are found primarily on macrophages, granulocytes and other large granular lymphocytes (Springer, T. A., et al., *Immunol. Rev.* 68:111–135 (1982); Keizer, G., et al., *Eur. J. Immunol.* 15:1142–1147 (1985)).

The LFA-1 glycoprotein family is composed of heterodimers, each containing an alpha-subunit which is non-covalently associated with a beta-subunit. The alpha-subunits of the family have been found to differ from one another and are designated CD11a, CD11b, and CD11c, respectively. The glycosylated alpha-subunits have approximate molecular weights of 180, 170, and 150 kd, respectively. In contrast, the beta-subunit of the LFA-1 family of adhesion receptors has been found to be identical, and to have a molecular weight of 95 kd (Sanchez-Madrid, F., et al., *J. Exper. Med.* 158:1785–1803 (1983); Keizer, G. D., et al., *Eur. J. Immunol.* 15:1142–1147 (1985); Springer, T., *Fed. Proc.* 44:2660–2663 (1985); Sanchez-Madrid, F., et al., *J. Exper. Med.* 158:586–602 (1983)).

Although the alpha-subunits of the glycoproteins do not exhibit the extensive homology shared by the beta-subunits, close analysis of the alpha-subunits of the glycoproteins has revealed that there are substantial similarities between them. Reviews of the similarities between the alpha and beta-subunits of the adhesion molecule glycoprotein family are provided by Sanchez-Madrid, F., et al. (*J. Exper. Med.* 158:586–602 (1983); *J. Exper. Med.* 158:1785–1803 (1983); Miller, L. J., et al., *J. Immunol.* 138:2381–2383 (1987)).

The importance of the LFA-1 family of receptors was initially recognized in studies which showed the ability of monoclonal anti-bodies (which were capable of binding to either the specific alpha-subunits, or the common beta-subunit) to inhibit adhesion-dependent leukocyte functions (Sanchez-Madrid, F., et al., *Proc. Natl. Acad. Sci. USA* 79:7489–7493 (1982); Beller, D. I., et al., *J. Exper. Med.* 156:1000–1009 (1982)).

Recently, a group of individuals has been identified who are unable to express normal amounts of any member of the Mac-1 adhesion protein family on their leukocyte cell surfaces. This disease has been termed "Leukocyte Adhesion Deficiency" or "LAD" and is characterized by chronic and recurring infections, as well as other clinical symptoms (Anderson, D. C., et al., *Fed. Proc.* 44:2671–2677 (1985); Anderson, D. C., et al., *J. Infect. Dis.* 152:668–689 (1985)). Leukocytes from LAD patients display in vitro defects which were similar to those observed when leukocytes of normal individuals were antagonized by antibody specific for members of the LFA-1 family. LAD patients were found to be unable to mount a normal immune response. This failure was found to be due to an inability of the leukocytes of LAD patients to adhere to cellular and extracellular substrates (Anderson, D. C., et al., *Fed. Proc.* 44:2671–2677 (1985); Anderson, D. C., et al., *J. Infect. Dis.* 152:668–689 (1985)). These studies show that inflammatory reactions are mitigated when leukocytes are unable to adhere in a normal fashion due to the lack of functional adhesion molecules on their cell surface.

Thus, in summary, the ability of leukocytes to maintain the health and viability of an animal requires that they be capable of adhering to other cells (such as endothelial cells) and proteins (such as iC3b). This adherence has been found to require contacts which involve specific receptor molecules present on the leukocyte surface of the leukocytes. These cell surface receptor molecules have been found to be highly related to one another. Humans whose leukocytes lack these cell surface receptor molecules exhibit chronic and recurring infections, as well as other clinical symptoms.

Since leukocyte adhesion is involved in the process through which foreign tissue is identified and rejected, an understanding of this process is of significant value in the fields of organ transplantation, tissue grafts, allergy and oncology.

SUMMARY OF THE INVENTION

The present invention relates to leukocyte cell surface adhesion receptor molecules, and in particular, to the cloning and expression of the alpha-subunit of the Mac-1 receptor molecule through the use of recombinant DNA technology. The invention pertains to the adhesion molecule itself, to functional fragments of the molecule, to nucleic acid (i.e., DNA, and especially cDNA) capable of encoding these receptor molecules, and to plasmids which contain such nucleic acid sequences. The present invention additionally encompasses methods for producing the receptor molecules which employ recombinant DNA technology.

In detail, the invention pertains to Mac-1 alpha-subunit, or a functional derivative thereof, substantially free of natural contaminants.

The invention further pertains to the above Mac-1 alpha-subunit or the functional derivative thereof, which is additionally capable of binding to a molecule present on the surface of a cell.

The invention also includes the above Mac-1 alpha-subunit molecule, wherein the molecule contains at least one polypeptide selected from the group consisting of:

| | |
|---|---|
| a. | A-N-Q-R-G-S-L; |
| b. | M-E-Q-L-K-K-S; |
| c. | T-D-G-E-K-F-G; |
| d. | G-V-F-L-Y-T-S; |
| e. | V-D-V-D-S-S-N-G-S-T; |
| f. | D-V-N-G-D-K-L-T-D-V-A; |
| g. | D-L-T-M-D-G-L-V-D-L; |
| h. | Y-I-L-T-S-H-N; |
| i. | C-Q-D-D-L-S-I; |
| j. | T-I-Q-N-Q-L-R; |
| k. | V-Q-S-L-V-L-G; |
| l. | Y-Q-H-I-G-L-V; |
| m. | L-F-T-A-L-F-P; and |
| n. | F-S-L-V-G-T-P; |

The invention also includes a recombinant DNA molecule capable of expressing either the Mac-1 alpha-subunit or a functional derivative thereof.

The invention also provides a method for recovering Mac-1 alpha-subunit in substantially pure form which comprises the steps:

(a) solubilizing Mac-1 alpha-subunit from the membranes of cells expressing Mac-1 alpha-subunit, to form a solubilized Mac-1 alpha-subunit preparation, (b) introducing the solubilized Mac-1 alpha-subunit preparation to an affinity matrix, the matrix containing immobilized antibody capable of binding to Mac-1 alpha-subunit, (c) permitting the Mac-1 alpha-subunit to bind to the antibody of the affinity matrix, (d) removing from the matrix any compound incapable of binding to the antibody and (e) recovering the Mac-1 alpha-subunit in substantially pure form by eluting the Mac-1 alpha-subunit from the matrix.

The invention also provides a method for treating inflammation resulting from a response of the non-specific defense system (such as asthma; adult respiratory distress syndrome; multiple organ injury syndrome secondary to septicemia; multiple organ injury syndrome secondary to trauma; reperfusion injury of tissue; acute glomerulonephritis; reactive arthritis; dermatosis with acute inflammatory components; a central nervous system inflammatory disorder; thermal injury; hemodialysis; leukapheresis; ulcerative colitis; Crohn's disease; necrotizing enterocolitis; granulocyte transfusion associated syndrome; and cytokine-induced toxicity) in a mammalian subject which comprises providing to a subject in need of such treatment an anti-inflammatory agent, in an amount sufficient to suppress said inflammation; wherein said anti-inflammatory agent is selected from the group consisting of: the Mac-1 alpha-subunit; and a functional derivative of the Mac-1 alpha-subunit.

The invention also pertains to the above method which additionally comprises the co-administration of an agent selected from the group consisting of: the Mac-1 beta-subunit, and a functional derivative of the Mac-1 beta-subunit.

BRIEF DESCRIPTION OF THE FIGURES

FIGS. 2A–H show the nucleotide and cDNA-derived amino acid sequence of the alpha-subunit of Mac-1. The putative N-glycosylation sites are underlined. The signal sequence and the putative transmembrane region are indicated by a dotted line. The termination condon is labeled with an asterisk. Boxes in the 3' untranslated region show the polyadenylation signal sequences. Arrows mark the boundaries of a potential intron spliced out of some of the cDNAs.

FIG. 3 shows Mac-1 α homologous repeats. Common residues are boxed. The three repeats containing putative divalent cation-binding sites (V–VII) are aligned with additional N-terminal related sequences lacking the putative $Ca^{++}$ or $MG^{++}$-binding sites (I–IV). based on the frequency of each residue in the seven repeats of the α-subunits of Mac-1 and of other integrins (p150,95, the fibronectin receptor, the vitronectin receptor and the platelet glycoprotein IIb) ((Corbi, A. et al., *EMBO J.* 6:4023–4028 (1987)), 12–14), consensus sequences were derived for the regions flanking the putative divalent cation-binding sites. Consensus residues were defined as those appearing in at least 30% of the analyzed sequences. The consensus divalent cation-binding sequence and the coordination axes of the residues ligating the divalent cation are based on the sequence and the 3-dimensional structure of the $Ca^{2+}$ and $Mg^{2+}$-binding proteins parvalbumin, troponin C and calmodulin (38) and are shown below the alignments of the seven repeats.

FIGS. 4A–J show a comparison of the primary structure of the α-subunits of Mac-1, p150,95, vitronectin receptor, fibronectin receptor, and glycoprotein IIb. Identities between Mac-1 and the rest of the integrin α-subunits are boxed. The putative divalent cation-binding sites and the conversed flanking sequences are underlined by continuous and dotted lines, respectively. The putative transmembrane regions are indicated by TM.

FIGS. 5A–B show a comparison of the sequences of the leukocyte specific domain of Mac-1 alpha-subunit and p150, 95 alpha-subunit with the A repeats of von Willebrand factor, complement component C2 and factor B. Common residues between the sequences of Mac-1 α and/or p150,95 α and the rest of the proteins are boxed. The alignments were performed as described under Experimental Procedures.

DESCRIPTION OF THE PREFERRED EMBODIMENTS

Figure 1:
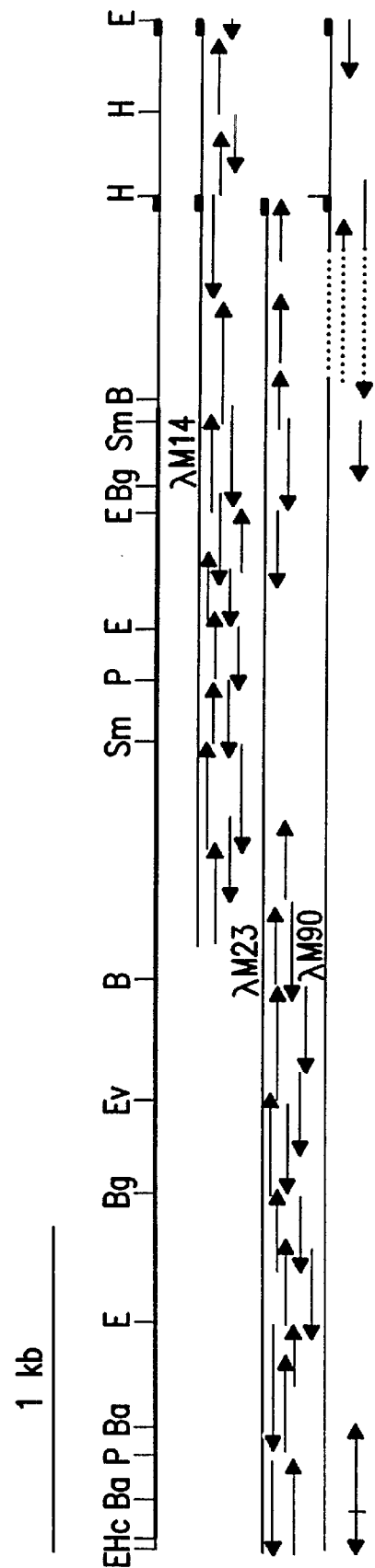
FIG. 1 shows the restriction map of Mac-1 alpha-subunit cDNA clones and sequencing strategy. The thick line represents the coding region of the cDNA. The polyadenylation signals are shown as black boxes. The regions deleted in λM90 is indicated as a dotted line. The indicated restriction sites are Bal I (B), Bam HI (Ba), Bgl II (Bg), Eco RI (E), Eco RV (Ev), Hinc II (Hc), Hind III (H), Sma I (S), and Pst I (P).

I. The Nature of the Leukocyte Adhesion Proteins of the Mac-1 Family

The three leukocyte adhesion proteins Mac-1, p150,95, and LFA-1 differ in function and in expression on leukocyte subpopulations. Mac-1 and p150,95 are expressed on neutrophils, and monocytes (Springer, T. A., et al., In: *Biochemistry of Macrophages* (CIBA Symposium 118); Pitman, London, pp. 102–126 (1986)). During differentiation of blood monocytes into tissue macrophages, expression of p150,95 is greatly increased and Mac-1 expression is decreased (Schwarting, R., et al., *Blood* 65:974–983 (1985); Hogg, N., et al., *Eur. J. Immunol.* 16:240–248 (1986)). p150,95 is also expressed on certain types of activated T and B lymphocytes, but is not expressed on these cells in the blood (Kaligaris-Cappio, F., et al., *Blood* 66:1035–1042 (1985); Miller, L. J., et al., *J. Immunol.* 137:2891–2900 (1986); Keizer, G. D., et al., *J. Immunol.* 138:3130–3136 (1987)).

LFA-1 is present on all leukocytes except a subset of macrophages. Monoclonal antibody blocking studies have shown that LFA-1 is important in T-lymphocyte-mediated killing, T helper lymphocyte responses, natural killing, and antibody-dependent killing (Springer, T. A., et al., *Ann. Rev. Immunol.* 5:223–252 (1987)). Adhesion to the target cell is a step which is blocked by antibodies against LFA-1. Functional studies have suggested that LFA-1 interacts with several ligands, one of which is ICAM-1 (Rothlein, R., et al., *J. Immunol.* 137:1270–1274 (1986)).

Mac-1 and p150,95 are expressed in an intracellular, vesicular compartment in circulating neutrophils and monocytes which is mobilized to the cell surface by inflammatory mediators (Todd, R. F., et al., *J. Clin. Invest.* 74:1280–1290 (1984); Springer, T. A., et al., In: *Biochemistry of Macrophages* (CIBA Symposium 118), Pitman, London, pp. 102–126 (1986); Lanier, L. L., et al., *Eur. J. Immunol.* 15:713–718 (1985); Yancey, K. B., et al., *J. Immunol.* 135:465–470 (1985)). This mobilization correlates with increased adhesiveness (Anderson, D. C., et al., *Ann. Rev. Med.* 38:175–194 (1987)). Mac-1 α-subunit message was detected in blood monocytes and PMA-induced myeloid cell lines, but not in cells of the T or B lineages, correlating with Mac-1 protein surface expression.

Some cytotoxic T lymphocyte clones have been found to express similar quantities of p150,95 and LFA-1. Monoclonal antibodies to the LFA-1 and p150,95 alpha-subunits inhibit killing by such CTL clones to similar extents and are additive in their inhibitory effects (Keizer, G. D., et al., *J. Immunol.* 138:3130–3136 (1987)). Furthermore, antibodies to p150,95 alpha-subunits have been shown to inhibit monocyte attachment to endothelium (Keizer, G. D., et al., *Eur. J. Immunol.* 17:1317–1322 (1987)).

Monoclonal antibodies to Mac-1 or p150,95 inhibit neutrophil aggregation and adherence to endothelial cells, protein-coated surfaces, bacteria, protozoan parasites, and fungi (Harlan, J. M., et al., *Blood* 66:167–178 (1985); Springer, T. A., et al., In: *Biochemistry of Macrophages* (CIBA Symposium 118), Pitman, London, pp. 102–126 (1986); Dana, N., et al., *J. Immunol.* 137:3259 (1986); Bullock, W. D., et al., *J. Exper. Med.* 165:195–210 (1987); Mosser, D. M., et al., *J. Immunol.* 135:2785–2789 (1985)).

Mac-1 (CD 11b/CD18) is a leukocyte adhesion heterodimeric glycoprotein which functions as a receptor for iC3b (CR3) in addition to its role in cell-cell and cell-substrate adhesive interactions (Belier, D. I., et al., *J. Exper. Med.* 156:1000–1009 (1982)). Detergent-soluble Mac-1 and p150,95 have been shown to be able to bind to iC3b-Sepharose® (Micklem, K. J., et al., *Biochem. J.* 231: 233–236 (1985)).

The α-subunit of Mac-1 is a transmembrane protein of 1137 residues with a long extracellular domain (1092 residues) and a 19-amino acid cytoplasmic tail. The extracellular domain contains 3 putative divalent cation-binding sequences and 19 potential N-glycosylation sites. The amino acid sequence of Mac-1 α shows that it is a member of the integrin superfamily; Mac-1 α shows 63% identity to the α-subunit of the leukocyte adhesion glycoprotein p150,95 and 25% to the α-subunits of the extracellular matrix receptors platelet glycoprotein IIb/IIIa, the fibronectin receptor and the vitronectin receptor. The Mac-1 α-subunit putative divalent cation-binding sites and the flanking regions exhibit a high degree of identity both to the p150,95 α-subunit (87% identity at the amino acid level) and to the rest of the integrin α-subunits (38%). The α-subunit of Mac-1, like the p150,95 α-subunit, contains a domain of 187 amino acids in the extracellular region which is absent in other integrins. This leukocyte or "L" domain is homologous to the A domains of van Willebrand factor, which in turn are homologous to regions of the C3-binding proteins factor B and C2. These findings draw attention to this region of Mac-1 as a potential binding site for iC3b.

The functional role of Mac-1 was first illustrated by the ability of anti-Mac-1 α-subunit monoclonal antibodies (MAb) to block the rosetting of iC3b-coated erythrocytes to macrophages and polymorphonuclear leukocytes (Beller, D. I. et al., *J. Exper. Med.* 156:1000–1009 (1982)), demonstrating that Mac-1 is indistinguishable from the complement receptor type three (CR3). Subsequently, the involvement of Mac-1 in inflammatory processes was evidenced by the inhibition of neutrophil aggregation and adhesion to endothelial cells by anti-Mac-1 α-subunit and anti-β-subunit-specific MAb (Anderson, D. C. et al., *J. Immunol.* 137:15–27 (1986); Dana, N. et al., *J. Immunol.* 137:3259–3263 (1986); Vedder, N. B. et al., *J. Clin. Invest.* 81:672–682 (1988)). Recent epitope mapping studies have suggested that the sites involved in iC3b-binding are distinct from those involved in neutrophil aggregation and adherence to protein-coated plastic (Anderson, D. C. et al., *J. Immunol.* 137:15–27 (1986); Dana, N. et al., *J. Immunol.* 137:3259–3263 (1986), Rosen, H. et al., *J. Exper. Med.* 166:1685–1701 (1987)). Therefore, Mac-1 appears to be a multivalent receptor with at least two independent adhesion-related functions.

The expression of functional activity of Mac-1 is regulated during leukocyte differentiation and activation. Differentiation and maturation of myelomonocytic cell lines results in increased Mac-1 expression (Miller, L. J. et al., *J. Immunol.* 137:2891–2900 (1986)), while blood monoctye differentiation into tissue macrophages is accompanied by a considerable decrease in the amount of Mac-1 on all cell surface (Hogg, N. et al., *Eur. J. Immunol.* 16:240–248 (19886)). The expression of Mac-1 on the surface of circulating meutrophils and monocytes is upregulated by inflammatory stimuli; Mac-1 is stored in an intracellular vesicular compartment which is rapidly mobilized to the cell surface by chemoattractants (Todd, R. F. et al., *J. Clin. Invest.* 74:1280–1290 (1984)); Miller, L. J. et al., *J. Clin. Invest.* 80:535–544 (1987)). Although the augmented expression of Mac-1 can lead to increased adhesiveness, qualitative changes after cell activation may also be important in regulation ligand binding (Detmers, P. A. et al., *J. Cell Biol.* 105:1137–1145 (1987)). Both the qualitative and quantitative changes may be important in regulation of leukocyte binding to post-capillary endothelium at inflammatory sites.

The N-terminal sequence of the murine and human Mac-1 α-subunits (Miller, L. J. et al., *J. Immunol.* 138:2381–2383 (1987); Springer, T. A. et al., *Nature* 314:540–542 (1985)) and a murine genomic clone encoding a short N-terminal exon (Sastre, L. et al., *Proc. Natl. Acad. Sci. (U.S.A.)* 83:5644–5648 (1986)) have been reported.

Most of the Mac-1 α-subunit is similar to the α-subunits of the extracellular matrix receptor integrins, with an additional domain which is related to the A repeats of von Willebrand factor and to two C3-binding proteins, Factor B and C2.

II. Cloning of the Mac-1 Alpha-subunit

Any of a variety of methods may be used to clone the Mac-1 alpha-subunit gene. One such method entails analyzing a shuttle vector library of cDNA inserts (derived from a Mac-1 alpha-subunit expressing cell) for the presence of an insert which contains the Mac-1 alpha-subunit gene. Such an analysis may be conducted by transfecting cells with the vector, and then assaying for Mac-1 alpha-subunit expression. Mac-1 alpha-subunit is preferably assayed using antibodies specific for the Mac-1 alpha-subunit. A preferred method for cloning the Mac-1 alpha-subunit gene entails determining the amino acid sequence of the Mac-1 alpha-subunit molecule, or tryptic peptides of the molecule. To accomplish this task, Mac-1 alpha-subunit molecules are preferably purified from producer cells by monoclonal antibody affinity chromatography and isolated by preparative sodium dodecyl sulfate-polyacrylamide gel electrophoresis ("SDS-PAGE") and electroelution (Miller, L. J., et al., *J. Immunol.* 138:2381–2383 (1987), which reference herein is incorporated by reference). The alpha-subunit molecules are fragmented as with cyanogen bromide, or with proteases such as papain, chymotrypsin, or trypsin (Oike, Y., et al., *J. Biol. Chem.* 257:9751–9758 (1982); Liu, C., et al., *Int. J. Pept. Protein Res.* 21:209–215 (1983)). Preferably, the alpha-subunit is proteolytically digested with trypsin. The resulting peptides are separated by reverse-phase HPLC and subjected to amino acid sequencing. To accomplish this task, the protein is, preferably, analyzed by automated sequenators. Although it is possible to determine the entire amino acid sequence of the Mac-1 alpha-subunit, it is preferable to determine the sequence of peptide fragments of the molecule. A preferred source of the Mac-1 alpha-subunit is the SKW3 cell line.

The sequence of amino acid residues in a peptide is designated herein either through the use of their commonly employed three-letter designations or by their single-letter designations. A listing of these three-letter and one-letter designations may be found in textbooks such as *Biochemistry*, Lehninger, A., Orth Publishers, New York, N.Y. (1970). When such a sequence is listed vertically, the amino terminal residue is intended to be at the top of the list, and the carboxy terminal residue of the peptide is intended to be at the bottom of the list. Similarly, when listed horizontally, the amino terminus is intended to be on the left end whereas the carboxy terminus is intended to be at the right end.

The residues of amino acids in a peptide may be separated by hyphens. Such hyphens are intended solely to facilitate the presentation of a sequence. As a purely illustrative example, the amino acid sequence designated:

-Gly-Ala-Ser-Pheindicates that an Ala residue is linked to the carboxy group of Gly, and that a Ser residue is linked to the carboxy group of the Ala residue and to the amino group of a Phe residue. The designation further indicates that the amino acid sequence contains the tetra-peptide Gly-Ala-Ser-Phe. The designation is not intended to limit the amino acid sequence to this one tetrapeptide, but is intended to include (1) the tetrapeptide having one or more amino acids linked to either its amino or carboxy end, (2) the tetrapeptide having one or more amino acid residues linked to both its amino and its carboxy ends, (3) the tetrapeptide having no additional amino acid residues.

Once one or more suitable peptide fragments have been sequenced, the DNA sequences capable of encoding them are examined. Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequences may be encoded by only a single oligonucleotide, frequently the amino acid sequence may be encoded by any of a set of similar oligonucleotides. Important, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

A suitable oligonucleotide, or set of oligonucleotides, which is capable of encoding a fragment of the Mac-1 alpha-subunit gene (or which is complementary to such an oligonucleotide, or set of oligonucleotides) is identified (using the above-described procedure), synthesized, and hybridized by means well known in the art, against a DNA or, more preferably, a cDNA preparation derived from human cells which are capable of expressing the Mac-1 alpha-subunit gene. Techniques of nucleic acid hybridization are disclosed by Maniatis, T., et al. (In: *Molecular Cloning. A Laboratory Manual,* Cold Spring Harbor Laboratories, Cold Spring Harbor, N.Y. (1982)), and by Haymes, B. D., et al. (In: *Nucleic Acid Hybridization. A Practical Approach,* IRL Press, Washington, D.C. (1985)), which references are herein incorporated by reference. The source of DNA or cDNA used will preferably have been enriched for Mac-1 alpha-subunit sequences. Such enrichment can most easily be obtained from cDNA obtained by extracting RNA from cells which produce high levels of the Mac-1 alpha-subunit.

Techniques such as, or similar to, those described above have successfully enabled the cloning of genes for human aldehyde dehydro-genases (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:8715–8719 (1985)).

Using the genetic code (Watson, J. D., In: *Molecular Biology of the Gene,* 3rd Ed., W. A. Benjamin, Inc., Menlo Park, Calif. (1977)), one or more different oligonucleotides can be identified, each of which would be capable of encoding the Mac-1 alpha-subunit tryptic peptides. The probability that a particular oligonucleotide will, in fact, constitute the actual Mac-1 alpha-subunit-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the Mac-1 alpha-subunit tryptic peptide sequences is identified.

The oligonucleotide, or set of oligonucleotides, containing the theoretical "most probable" sequence capable of encoding the Mac-1 alpha-subunit fragments is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the Mac-1 alpha-subunit gene (Maniatis, T., et al., *Molecular Cloning A Laboratory Manual,* Cold Spring Harbor Press, Cold Spring Harbor, N.Y. (1982).

Thus, in summary, the actual identification of Mac-1 alpha-subunit peptide sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe to identify and isolate the Mac-1 alpha-subunit gene.

Single stranded oligonucleotide molecules complementary to the "most probable" Mac-1 alpha-subunit tryptic peptide encoding sequences were synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression,* Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers.

It is possible to clone the Mac-1 alpha-subunit gene from eukaryotic DNA preparations suspected of containing this gene. To identify and clone the gene which encodes the Mac-1 alpha-subunit protein, a DNA, or more preferably a cDNA, library is screened for its ability to hybridize with the oligonucleotide probes described above. Suitable DNA preparations (such as human genomic DNA) are enzymatically cleaved, or randomly sheared, and ligated into recombinant vectors. The ability of these recombinant vectors to hybridize to the above-described oligonucleotide probes is then measured. Procedures for hybridization are disclosed, for example, in Maniatis, T., *Molecular Cloning A Laboratory Manual,* Cold Spring Harbor Press, Cold Spring Harbor, N.Y. (1982) or in Haymes, B. T., et al., *Nucleic Acid Hybridization a Practical-Approach,* IRL Press, Oxford, England (1985). Vectors found capable of such hybridization are then analyzed to determine the extent and nature of the Mac-1 alpha-subunit sequences which they contain. Based purely on statistical considerations, a gene such as that which encodes the Mac-1 alpha-subunit molecule could be unambiguously identified (via hybridization screening) using an oligonucleotide probe having only 18 nucleotides.

The cloned Mac-1 alpha-subunit gene, obtained through the method described above, may be operably linked to an expression vector, and introduced into prokaryotic or eukaryotic cells to produce the Mac-1 alpha-subunit protein. Techniques for such manipulations are disclosed by Maniatis, T., et al., supra, and are well known in the art.

III. The Expression of the Mac-1 Alpha-subunit

The present invention derives, in part, from the discovery of the cDNA sequence which encodes the alpha-subunit of the Mac-1 molecule. By operably linking this sequence (or a fragment of this sequence) to a functional promoter, it is possible to direct the expression of the alpha-subunit of Mac-1 (or a functional derivative thereof) in a cell, or organism.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Regulatory regions in eukaryotic cells will in general include a promoter region sufficient to direct the initiation of RNA synthesis.

Two DNA sequences (such as a promoter region sequence and a Mac-1 alpha-subunit-encoding sequence) are said to be operably linked if the nature of the linkage between the two DNA sequences does not (1) result in the introduction of a frame-shift mutation, (2) interfere with the ability of the promoter region sequence to direct the transcription of the Mac-1 alpha-subunit-encoding sequence, or (3) interfere with the ability of the Mac-1 alpha-subunit-encoding sequence to be transcribed by the promoter region sequence. Thus, a promoter region would be operably linked to a DNA sequence if the promoter were capable of effecting transcription of that DNA sequence.

The present invention encompasses the expression of the Mac-1 alpha-subunit (or a functional derivative thereof) in either prokaryotic or eukaryotic cells. To express the Mac-1 alpha-subunit (or a functional derivative thereof) in a prokaryotic cell (such as, for example, E. coli, B. subtilis, Pseudomonas, Streptomyces, etc.), it is necessary to operably link the Mac-1 alpha-subunit-encoding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene of pBR322, and the CAT promoter of the chloramphenicol acetyl transferase gene of pPR325, etc. Examples of inducible prokaryotic promoters include the major right and left promoters of bacteriophage λ ($P_L$ and $P_R$), the trp, recA, lacZ, lacI, and qal promoters of E. coli, the α-amylase (Ulmanen, I., et al., J. Bacteriol. 162:176–182 (1985)) and the σ-28-specific promoters of B. subtilis (Gilman, M. Z., et al., Gene 32:11–20 (1984)), the promoters of the bacteriophages of Bacillus (Gryczan, T. J., In: The Molecular Biology of the Bacilli, Academic Press, Inc., NY (1982)), and Streptomyces promoters (Ward, J. M., et al., Mol. Gen. Genet. 203:468–478 (1986)). Prokaryotic promoters are reviewed by Glick, B. R., (J. Ind. Microbiol. 1:277–282 (1987)); Cenatiempo, Y. (Biochimie 68:505–516 (1986)); and Gottesman, S. (Ann. Rev. Genet. 18:415–442 (1984)).

Proper expression in a prokaryotic cell requires the presence of a ribosome binding site upstream of the gene-encoding sequence. Such ribosome binding sites are disclosed, for example, by Gold, L., et al. (Ann. Rev. Microbiol. 35:365–404 (1981)).

If expression is desired in a eukarotic cell, such as yeast, fungi, mammalian cells, or plant cells, then it shall be necessary to employ a promoter capable of directing transcription in such a eukaryotic host. Preferred eukaryotic promoters include the promoter of the mouse metallothionein I gene (Hamer, D., et al., J. Mol. Appl. Gen. 1:273–288 (1982)); the TK promoter of Herpes virus (McKnight, S., Cell 31:355–365 (1982)); the SV40 early promoter (Benoist, C., et al., Nature (London) 290:304–310 (1981)); the yeast gal4 gene promoter (Johnston, S. A., et al., Proc. Natl. Acad. Sci. (USA) 79:6971–6975 (1982); Silver, P. A., et al., Proc. Natl. Acad. Sci. (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the Mac-1 alpha-subunit (or a functional derivative thereof) does not contain any intervening codons which are capable of encoding a methionine (i.e., AUG). The presence of such codons results either in a formation of a fusion protein (if the AUG codon is in the same reading frame as the Mac-1 encoding DNA sequence) or a frame-shift mutation (if the AUG codon is not in the same reading frame as the Mac-1 encoding sequence).

A DNA sequence which encodes the Mac-1 protein (or a functional derivative thereof) when operably linked to a functional promoter is preferably introduced into a recipient cell by any of a variety of suitable means: transformation, transfection, conjugation, protoplast fusion, electroporation, etc.

The Mac-1 alpha-subunit-encoding sequence and an operably linked promoter may be introduced into a recipient cell either as a non-replicating DNA (or RNA) molecule, which may either be a linear molecule or, more preferably, a closed covalent circular molecule. Since such molecules are incapable of autonomous replication, the expression of the Mac-1 alpha-subunit polypeptide may occur through the transient expression of the introduced sequence. Alternatively, permanent expression may occur through the integration of the introduced sequence into the host chromosome.

Preferably, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in E. coli (such as, for example, pBR322, ColE1, pSC101, pACYC 184, πVX. Such plasmids are, for example, disclosed by Maniatis, T., et al. (In: Molecular Cloning, A Laboratory Manual, Cold Spring Harbor Press, Cold Spring Harbor, N.Y. (1982)). Bacillus plasmids include pC194, pC221, pT127, etc. Such plasmids are disclosed by Gryczan, T. (In: The Molecular Biology of the Bacilli, Academic Press, NY (1982), pp. 307–329). Suitable Strentomyces plasmids include pIJ101 (Kendall, K. J., et al., J. Bacteriol. 169:4177–4183 (1987)), and streptomyces bacteriophages such as øC31 (Chater, K. F., et al., In: Sixth International Symposium on Actinomyceteles Biology, Akademiai Kaido, Budapest, Hungary (1986), pp. 45–54). Pseudomonas plasmids are reviewed by John, J. F., et al. (Rev. Infect. Dis. 8:693–704 (1986)), and Izaki, K. (Jpn. J. Bacteriol. 33:729–742 (1978)).

Preferred eukaryotic plasmids include BPV, vaccinia, SV40, 2-micron circle, etc., or their derivatives. Such plasmids are well known in the art (Botstein, D., et al., Miami Wntr. Symp. 19:265–274 (1982); Broach, J. R., In: The Molecular Biology of the Yeast Sacchaaromyces: Life Cycle and Inheritance, Cold Spring Harbor Laboratory, Cold Spring Harbor, N.Y., p. 445–470 (1981); Broach, J. R., Cell 28:203–204 (1982); Bollon, D. P., et al., J. Clin. Hematol. Oncol. 10:39–48 (1980); Maniatis, T., In: Cell Biology: A Comprehensive Treatise, Vol. 3, Gene Expression, Academic Press, NY, pp. 563–608 (1980)).

IV. Uses of the Mac-1 Alpha-subunit, or Fragments Thereof

The present invention provides the nucleic acid and protein sequences of the alpha-subunit of the Mac-1 receptor molecule. This discovery permits the use of recombinant DNA technology to produce the Mac-1 alpha-subunit molecule. As discussed further below, one embodiment of the present invention pertains to the use of the alpha-subunit of the Mac-1 molecule by itself, as an anti-inflammatory agent. In a preferred embodiment, the alpha-subunit of the Mac-1 molecule will be used in combination with its beta-subunit. Most preferably in a combination which creates a functional Mac-1 alpha and beta heterodimer. Most preferably, such heterodimers will container recombinant Mac-1 alpha subunits or their functional derivatives. Such a combination may be produced using a variety of methods. For example, the beta-subunit of Mac-1 may be produced separately from the Mac-1 alpha-subunit, and the two molecules may then be mixed together. It is, however, preferable to produce both the alpha and beta-subunits of Mac-1 in the same host cell in order to facilitate their self-assembly into the Mac-1 heterodimer receptor molecule. The beta-subunit of Mac-1 (which is common to LFA-1, and p150,95) may be produced either by chemical synthesis, or by recombinant DNA techniques (Kishimoto, T. K., et al., *Cell* 48:681–690 (1987)). The cloning of the beta-subunit of Mac-1 is further disclosed in commonly assigned, co-pending U.S. patent application Ser. No. 019,440, filed on Feb. 26, 1987, which application is herein incorporated by reference.

One aspect of the present invention relates to the discovery of the nucleic acid and protein sequences of the alpha-subunit of the Mac-1 receptor molecule. This discovery permits the use of recombinant DNA technology to produce functional derivatives of the Mac-1 alpha-subunit which may function as antagonists of cellular adhesion. As used herein, an "antagonist of cellular adhesion" is meant to refer to any molecule capable of inhibiting the process of cell-cell or cell-substrate adhesion. It is possible to determine whether a particular compound is an antagonist by performing an assay of monocyte adhesion to endothelial cells, neutrophil aggregation, or iCb3 rosetting of neutrophils. Suitable assays of cellular adhesion are disclosed, for example, by Anderson, D. C., et al. (*J. Immunol.* 137:15–27 (1986)) and by Keizer, G. D., et al. (*Eur. J. Immunol.* 17:1317–1322 (1987)) which references are herein incorporated by reference. Antagonists of cellular adhesion may be employed as anti-inflammatory agents.

As used herein, a "functional derivative" of the alpha-subunit of Mac-1 is a compound which possesses a biological activity (either functional or structural) that is substantially similar to a biological activity of the alpha-subunit of Mac-1. Examples of biological activities include the ability to bind to the natural ligand of Mac-1, or well on the ability to bind to the β-subunit of the LFA family of glycoproteins. Such binding would inhibit adhesion related events such as granulocyte migration through endothelium, granulocyte aggregation and iCb3 rossetting. A molecule is said to be "substantially similar" to another molecule if both molecules have substantially similar structures or if both molecules possess a similar biological activity. The "functional derivatives" of the alpha-subunit of Mac-1 include both "fragments" and "variants" of the Mac-1 alpha-subunit. The term "fragment of the alpha-subunit of Mac-1" is meant to refer to any polypeptide subset of that molecule. The term "variant of the alpha-subunit of Mac-1" is meant to refer to a molecule substantially similar in structure to either the entire molecule, or to a fragment thereof provided that the "variant" has at least one biological activity that is either similar to an activity of the alpha-subunit of Mac-1 or inhibitory to an activity of Mac-1. Thus, provided that a molecule possesses at least one biological activity that is either similar to an activity of Mac-1 or inhibitory to such an activity, it is considered a "variant" of the alpha-subunit Mac-1, as that term is used herein, even if one of the molecules contains one or more amino acids not found in the other, or if the sequences of amino acid residues in the two molecules are not identical. Thus, for example, a compound lacking (or containing) one or more amino acid residues found (or not found) in the alpha-subunit of Mac-1 would be considered to be a variant of the alpha-subunit of Mac-1 if that compound possessed a biological activity similar to (or inhibitory to) a biological activity of the alpha-subunit of Mac-1. The term "biological activity" is intended to encompass "catalytic" as well as "structural" activity (i.e., the capacity to bind to another molecule, such as the beta-subunit of Mac-1, anti-alpha-subunit Mac-1 antibody, iCb3, or another natural ligand of Mac-1), etc.

The present invention provides a method for producing functional derivatives of the alpha-subunit of the Mac-1 molecule. To obtain such derivatives, it is necessary only to mutagenize a DNA, RNA, or (more preferably) the cDNA sequence which encodes the Mac-1 alpha-subunit. Mutagenesis can either be random, or site specific. Further, mutagenesis may either be spontaneous or induced using chemical, radioactive, or recombinant techniques.

The scope of the present invention is further intended to include functional derivatives which lack certain amino acid residues, or which contain altered amino acid residues, so long as such derivatives exhibit the capacity to enhance or inhibit cellular adhesion.

Chemical mutagens include base analogs (such as, for example, 5-bromouracil, or 2-aminopurine); deaminating agents (such as, for example, nitrous acid, hydroxylamine, etc.); alkylating agents (such as, for example, methyl methanesulphonate, nitrosoguanidine, etc.); or intercalating agents (such as, for example, acridine orange, ethidium bromide, psoralen, etc.). Radiation-induced mutation can be caused by agents such as ultraviolet light, gamma, X-ray, etc. Techniques for mutagenizing nucleic acid molecules may be found in Miller, J. H. (In: *Experiments in Molecular Biology*, Cold Spring Harbor Laboratory, Cold Spring Harbor, N.Y. (1972)), and Silhavy, T. J., et al. (In: *Experiments with Gene Fusions*, Cold Spring Harbor Laboratory, Cold Spring Harbor, N.Y. (1984)).

Site-specific mutagenesis may be employed to produce specific mutations at desired sites of the nucleic acid encoding the Mac-1 alpha-subunit. In brief, such procedures generally entail the synthesis of a synthetic oligonucleotide having a desired and defined DNA sequence. Methods for synthesizing such oligonucleotides are disclosed by Itakura, K., et al. (*Ann. Rev. Biochem.* 53:323–356 (1984)). A nucleic acid molecule which encodes the Mac-1 alpha-subunit protein, or a functional derivative thereof, is generally subcloned onto a double-stranded vector such as M13, øX174, etc., whose single strands may be separated one from another. A single strand of the vector is then incubated in the presence of the sythetic oligonucleotide. Since the DNA of the oligonucleotide is controllably defined, it is possible to construct an oligonucleotide capable of base pairing with any region of the Mac-1 alpha-subunit-encoding nucleic acid. Once base pairing has occurred between the oligonucleotide and the single-stranded plasmid, it is possible to extend the oligonucleotide using DNA polymerase to create a double-stranded DNA molecule which may then be sealed by DNA ligase. When this double-stranded DNA molecule is introduced into a cell, semi-conservative DNA replication will result in the production of progeny molecules in which the DNA sequence of the oligonucleotide fragment has been incorporated into the Mac-1 alpha-subunit-encoding sequences.

The Mac-1 alpha subunit of the present invention, or its functional derivatives, may alternatively be prepared by synthetic chemical method using the well-known Merriefield or other techniques of peptide synthesis. Alternatively, such molecules may also be prepared by chemical synthesis of nucleic acid molecules (using, for example, phosphodiester synthesis techniques), which, upon expression, will result in their production.

Thus, if one desired to introduce a point mutation, and exogenous DNA sequence into a specific site in the Mac-1-encoding sequence, or to create a deletion of nucleotides normally present in such a sequence, one would design an oligonucleotide fragment which contained (or lacked) the mutation or sequence, and then pursue the above-described procedure. In order to introduce such a mutation or exogenous DNA sequence into a particular region of the Mac-1 alpha-subunit-encoding nucleic acid, it is necessary to surround the mutation or the exogenous DNA sequence with flanking DNA sequences that are complementary to the DNA sequence of the region whose mutagenesis is desired. (Jenkins, F., et al., *Bioessays* 5:244–247 (1986); Doerfler, W., *Angew. Chem. Int. Ed. Engl.* 23:919–931 (1984); Kaina, B., *Biol. Zentralbl.* 99:513–531 (1980); Kunkel, *Proc. Natl. Acad. Sci.* (*USA*) 82:488–492 (1985); Nisbet, I. T., et al., *Gene Anal. Tech.* 2:23–29 (1985); Hines, J. C., et al., *Gene* 11:207–218 (1980); Messing, J., et al., *Nucl. Acid. Res.* 9:309 (1981)).

Mutations can also be produced through the application of recombinant DNA technology. For example, the nucleotide sequence of a nucleic acid molecule which encodes the Mac-1 alpha-subunit can be scanned to identify oligonucleotide sites which are recognizable by restriction endonucleases. Such endonucleases can then be used to specifically cleave the nucleic acid sequence at a recognized site. By using a restriction endonuclease that recognizes (and cleaves at) two positions in the Mac-1-encoding sequence, it is possible to excise a fragment of the Mac-1 alpha-subunit-encoding sequence. Alternatively, it is possible to use two different endonucleases for this purpose. By incubating the cleaved molecules in the presence of DNA ligase, it is possible to reseal the Mac-1 alpha-subunit-encoding sequences to form a single sequence (which lacks the excised fragment). If no appropriate restriction endonuclease recognition sites exist in the Mac-1 alpha-subunit-encoding sequences, then such sites may be introduced into the sequences by the site-specific mutagenesis procedure described above.

Mutations may alternatively be introduced by cleaving the Mac-1 alpha-subunit-encoding sequence and "nibbling" the free termini with an exonuclease. By such treatment it is possible to introduce not only deletions, but frame-shift and other types of mutations. This technique is, moreover, capable of introducing novel restriction endonuclease sites into the Mac-1 alpha-subunit-encoding sequence. Methods for using restriction endonucleases, DNA ligases, and exonucleases are disclosed, for example, by Maniatis, T., et al. (In: *Molecular Cloning, A Laboratory Manual,* Cold Spring Harbor Laboratory, Cold Spring Harbor, N.Y. (1982)).

Recombinant DNA techniques may also be used to produce fusion proteins composed of the Mac-1 alpha-subunit protein (or a functional derivative thereof) and a novel polypeptide. This novel polypeptide is not limited to any particular polypeptide and may comprise either a single amino acid or any set or permutation of amino acids. Such fusion molecules may be produced by ligating a DNA sequence which encodes the novel polypeptide to a DNA sequence which encodes the Mac-1 alpha-subunit (or a functional derivative thereof), in a manner which does not introduce a frame-shift mutation. Examples of preferred polypeptides which may be fused to the Mac-1 alpha-subunit gene (or a functional derivative thereof) include eukaryotic or prokaryotic signal sequences (Gilbert, W., et al., U.S. Pat. No. 4,411,994; Casadaban, M., et al., *Proc. Natl. Acad. Sci.* (*USA*) 76:4530–4533 (1979)), or polypeptides which extend (or diminish) the stability, biological half-life, or potency of the Mac-1 alpha-subunit (or a functional derivative thereof). An excellent review of the methodology of gene fusions is provided by Silhavy, T. J., et al. (In: *Experiments with Gene Fusions,* Cold Spring Harbor Laboratory, Cold Spring Harbor, N.Y. (1984)).

Antibodies (especially monoclonal antibodies) may be elicited in response to immunization with fragments of the Mac-1 alpha-subunit or to the recombinant Mac-1 alpha subunit. Such antibodies can be used to prevent the binding of some leukocytes to endothelial cells, and thus may be employed as anti-inflammatory agents.

Using the methods described above, fragments of the Mac-1 alpha-subunit may be prepared and assayed to determine whether they are antagonists of cellular adhesion. Fragments found to be antagonists of cellular adhesion may be employed as anti-inflammatory agents in accordance with the present invention.

The present invention derives in part from the discovery that the adhesion ability of circulating neutrophils and monocytes results from interactions involving the Mac-1 receptor molecule. Since cellular adhesion is required in order that such cells may migrate to sites of inflammation and/or carry out various effector functions contributing to inflammation, agents which inhibit such cellular adhesion will attenuate or prevent inflammation. The Mac-1 receptor molecule is present on the surface of neutrophils and monocyte cells. The adhesion of these cells to plastic surfaces, or to monolayers of endothelial cells, is mediated by the Mac-1 receptor molecule. In addition, the ability of monocytes to phagocytose foreign material has been found to be mediated by the Mac-1 receptor molecule. The receptor molecule has also been implicated as having a role in chemokinesis, and chemotaxis of monocytes.

Agents which interfere with the capacity of the Mac-1 receptor molecule to bind to its natural binding ligand are thus capable of impairing all of the above-described Mac-1-dependent functions. Hence, these agents may serve as anti-inflammatory agents in accordance with the present invention. Such agents include the Mac-1 alpha-subunit, Mac-1 (i.e., the heterodimer composed of alpha and beta-subunits), a composition composed of the non-associated Mac-1 alpha and beta subunits, and antibody capable of binding to the Mac-1 alpha-subunit, or to fragments of that subunit. In one embodiment of the present invention, such agents are composed of soluble Mac-1 alpha subunits or soluble functional derivatives thereof, and are able to interfere with or inhibit either the binding of natural Mac-1 alpha with its beta subunit, or inhibit the ability of Mac-1 to bind to any of its natural binding ligands. All of such agents may be used in accordance with the present invention. The anti-inflammatory agents of the present invention are capable of treating inflammation caused by a reaction of the non-specific defense system.

A "non-specific defense system reaction" is a response mediated by leukocyte cells incapable of immunological memory. Such cells include lymphocytes and macrophages. As used herein, inflammation is said to result from a response of the non-specific defense system, if the inflammation is caused by, mediated by, or associated with a reaction of the non-specific defense system. Examples of inflammation which result, at least in part, from a reaction of the non-specific defense system include inflammation associated with conditions such as: asthma, adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; cytokine-induced toxicity; and atherosclerosis.

Since Mac-1 is expressed on cells which are capable of binding to endothelial tissue, the administration of the Mac-1 alpha-subunit, or Mac-1 (alpha and beta-subunits) to a patient provides a means for imaging or visualizing endothelial tissue. Moreover, this procedure provides diagnostic information concerning the quantity and distribution of the binding ligands of the Mac-1 receptor molecule which are present on the visualized tissue. In such a use, the Mac-1 alpha-subunits (or Mac-1 alpha beta receptor molecules) are detectably labeled, through the use of radioisotopes, affinity labels (such as biotin, avidin, etc.) fluorescent labels, paramagnetic atoms, etc. Procedures for accomplishing such labeling are well known to the art. The antibodies (or fragments thereof) may be detectably labeled through the use of radioisotopes, enzyme labels, fluorescent labels, paramagnetic labels, electron-dense labels, toxin labels, etc. Preferred toxin labels include the diphtheria toxin, ricin, and cholera toxins. The administration of such labeled molecules into an individual will identify sites of inflammation. Such detectable labels can also be used to assay the status of a patient's immune system. Clinical application of antibodies in diagnostic imaging are reviewed by Grossman, H. B., *Urol. Clin. North Amer.* 13:465–474 (1986)), Unger, E. C. et al., *Invest. Radiol.* 20:693–700 (1985)), and Khaw, B. A. et al., *Science* 209:295–297 (1980)).

The ability of monocytes to migrate spontaneously to sites of inflammation is dependent upon Mac-1 (Keizer, G. D., et al., *Eur. J. Immunol.* 17:1317–1322 (1987)). Such migration may be inhibited by administrating Mac-1 alpha-subunits, or Mac-1 (alpha and beta-subunit) to a patient.

Similarly, the ability of monocytoid cells to adhere to endothelial cells, and the ability of monocytoid cells to undergo chemotaxis, chemokinesis, or phagocytosis has been found to be dependent upon Mac-1 (Keizer, G. D., et al., *Eur. J. Immunol.* 17:1317–1322 (1987)). Any of the anti-inflammatory agents of the present invention may be employed to inhibit such activites.

ICAMs (such as ICAM-1) are recognized by certain human viruses (particularly rhinoviruses of the major type (which bind to ICAM-1). These viruses bind to human cells by virtue of this recognition, and thereby mediate viral infection. Thus, a central step in the etiology of viral disease is the interaction between these cellular receptors and the virus.

Agents which suppress, compete with, or inhibit the ability of a virus to bind to an ICAM molecule thus have use in the treatment of viral (and particularly rhinoviral) infection.

One aspect of the present invention thus concerns the ability of the alpha-subunit of MAC-1 and its functional derivatives to interact with ICAM-1 and to thereby either prevent cell-viral attachment and viral infection, or to attenuate or diminish the severity or duration of such infection.

Of particular interest to the present invention are functional derivatives of the alpha-subunit of MAC-1 such as solubilized forms of the alpha-subunit of MAC-1, fragments of the alpha-subunit of MAC-1, etc. Such agents are preferably provided to a recipient patient as a heterodimer containing the molecule in association with a molecule of the beta-subunit of the CD-18 family. The above-described goal of treating viral infection may be accomplished with a single agent or with a combination of more than one agents.

For the purpose of treating viral infection, the above-described agent(s) of the present invention is to be provided to a recipient patient (for example, by intranasal means) at a dosage sufficient to permit the agent(s) to suppress, compete with, or inhibit the ability of a virus to bind to an ICAM molecule. Such a dosage shall, in general, be (for each agent provided) from 0.01 pg/kg patient weight to 1 mg/kg patient weight, although greater or lesser amounts can be employed.

For the purpose of treating viral infection, the administration of such agent(s) may be provided either "prophylactically" or "therapeutically." When provided prophylactically, the agent(s) are provided in advance of (i.e. prior to, at, or shortly after) the time of infection but in advance of any symptoms of viral infection. The prophylactic administration of the agent(s) serves to prevent or attenuate any subsequent infection. When provided therapeutically, the agent(s) are provided at (or shortly after) the onset of a symptom of actual viral infection (such as, for example, the appearance of virally induced nasal congestion, etc. or the detection of virus in bodily fluids, or the detection of antibodies, directed against the virus, in the serum of an infected patient, etc). The therapeutic administration of the agent(s) serves to attenuate any actual infection, and thus lessen its severity or duration.

V. Administration of the Mac-1 Alpha-Subunit

The therapeutic effects of Mac-1 alpha-subunit may be obtained by providing to a patient the Mac-1 receptor molecule ($\alpha$ and $\beta$-subunits), the entire Mac-1 alpha-subunit molecule, or any therapeutically active functional derivative thereof. These molecules may be obtained either synthetically, or through the use of recombinant DNA technology. Fragments of the Mac-1 receptor or its alpha-subunit may additionally be obtained by proteolysis. The therapeutic advantages of these molecules may be augmented through the use of functional derivatives which possess additional amino acid residues added to enhance coupling to carrier or to enhance activity.

The molecules of the present invention are said to be "substantially free of natural contaminants" if preparations which contain them are substantially free of materials with which these products are normally and naturally found.

In providing a patient with the therapeutic molecules of the present invention, the dosage of administered agent will vary depending upon such factors as the patient's age, weight, height, sex, general medical condition, previous medical history, etc. In general, it is desirable to provide the recipient with a dosage of Mac-1 alpha-subunit (or a functional derivative thereof) which is in the range of from about 1 pg/kg to 10 mg/kg (body weight of patient), although a lower or higher dosage may be administered.

The molecules of the present invention may be administered to patients intravenously, intramuscularly, subcutaneously, enterally, or parenterally. Administration may be by continuous infusion, or by single or multiple boluses.

The anti-inflammatory agents of the present invention are intended to be provided to recipient subjects in an amount sufficient to suppress inflammation. An amount is said to be sufficient to suppress inflammation if the dosage, route of administration, etc. of the agent are sufficient to attenuate or prevent inflammation. The anti-inflammatory agents of the present invention may be provided either prior to the onset of inflammation (so as to suppress the anticipated inflammation) or after the initiation of inflammation.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient. The molecules of the present invention can be formulated according to known methods to prepare pharmaceutically acceptable compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed.), Osol, A., ed., Mack, Easton, Pa. (1980). In order to form a pharmaceutically effective composition suitable for effective administration, such compositions will contain a therapeutically effective amount of Mac-1 alpha-subunit, or its fragments or functional derivatives, together with a suitable amount of carrier vehicle.

Additional pharmaceutical methods may be employed to control the duration of action. Controlled release preparations may be achieved through the use of polymers to complex or absorb Mac-1 alpha-subunit or its fragments or functional derivatives. The controlled delivery may be exercised by selecting appropriate macromolecules (for example, polyesters, polyamino acids, polyvinyl, pyrrolidone, ethylene vinyl-acetate, methylcellulose, carboxymethylcellulose, or protamine sulfate) and the concentration of macromolecules as well as the methods of incorporation in order to control release. Another possible method to control the duration of action by controlled release preparations is to incorporate Mac-1 alpha-subunit molecules, their fragments, or their functional derivatives, into particles of a polymeric material such as polyesters, polyamino acids, hydrogels, poly(lactic acid), or ethylene vinylacetate copolymers. Alternatively, instead of incorporating these agents into polymeric particles, it is possible to entrap these molecules in microcapsules prepared, for example, by coacervation techniques or by interfacial polymerization, for example, hydroxymethyl cellulose or gelatin-microcapsules and poly(methylmethacrylate) microcapsules, respectively, or in colloidal drug delivery systems, for example, liposomes, albumin microspheres, microemulsions, nanoparticles, and nanocapsules in macroemulsions. Such techniques are disclosed in Remington's Pharmaceutical Sciences (1980).

Having now generally described the invention, the same will be more readily understood through reference to the following examples which are provided by way of illustration, and are not intended to be limiting of the present invention, unless specified.

EXAMPLE 1

Protein Purification and Sequencing

The Mac-1α/β complex was purified from leukocyte Triton X-100 lysates by monoclonal antibody-affinity chromatography. Such purification was accomplished either through the use of the anti-Mac-1 α-subunit monoclonal antibody, LM2/1 (Miller, L. J. et al., *J. Immunol.* 138:2381–2383 (1987)), or, more preferably, through the use of anti-β monoclonal antibody, IB4.5 (Wright, S. D. et al., *Proc. Natl. Acad. Sci.* (*U.S.A.*) 80:5699–5703 (1983)). Affinity chromatography was accomplished by coupling the antibody to Sepharose® as described by (Miller, L. J. et al., *J. Immunol.* 138:2381–2383 (1987); Schneider, C. et al., *J. Biol. Chem.* 257:10766–10769 (1982)).

Lysates of Mac-1 expressing cells were prepared according to the method of (Miller, L. J. et al., *J. Immunol.* 138:2381–2383 (1987)). The lysate was passed through a 3 ml protein A-Sepharose pre-column connected in series with the 3.5 ml IB4.5 column after pre-washing of both columns with 50 ml of 0.5% Triton X-100, 0.5% sodium deoxycholate, 20 mM Tris-HCl pH 8. After loading the lysate, the column was washed with 40 ml of the same solution and the elution of the bound material was carried out by successive washings with buffers of increasing pH or ionic strength: 1) 10 ml of 0.1% Triton X-100, 0.1 M glycine pH 9; 2) 20 ml of 0.1% Triton X-100, 0.1 M glycine, pH 10; 3) 50 ml of 0.1% Triton X-100, 0.1 M TEA, pH 11.5; and 4) 40 ml of 0.14 M NaCl, 0.5% Triton X-100, 0.01 M Tris-HCl pH 8. SDS-PAGE of the fractions showed that most of the bound material was eluted at pH 11.5.

The α-subunit of Mac-1 was isolated by preparative SDS-polyacryamide gel electrophoresis of the affinity-purified antigen. After electroelution, the isolated α-subunit was precipitated with ethanol and reduced and alkylated. 50 μg of purified α-subunit was dissolved in 0.1 M ammonium bicarbonate, 0.1 mM calcium chloride, 0.3% zwittergent 3–14 and digested with 2% (w/W) trypsin at 37° C. for 6 hours, with further additions of 1% tyrpsin every 2 hours. The resulting peptides were separated by reverse-phase HPLC on a C4 column (Vydac) and eluted with a gradient of acetonitrile (0–60%) in 0.1% trifluoroacetic acid (TFA) for 2 hours. Collected fractions were concentrated and subjected to microsequencing on an applied Biosystems gas-liquid phase sequencer.

Immunoprecipitation with-subunit-specific monoclonal antibody showed that Mac-1 was the prevalent molecule eluted from the anti-β monoclonal antibody-Sepharose® column, as expected since neutrophils are the primary cell in the leukocyte lysate and express much more Mac-1 than LFA-1 or p150,95.

EXAMPLE 2

Isolation and Sequencing of cDNA Clones

The purified α-subunit was digested with trypsin and the resulting peptides separated by reverse-phase HPLC and subjected to protein micro-sequencing (Table I). Comparison of the Mac-1 α-subunit peptide sequences with the sequence of the p150,95 α-subunit (Corbi, A. et al., *EMBO J.* 6:4023–4028 (1987)) showed a high degree of similarity. Table I shows the tryptic peptides of the Mac-1 alpha-subunit, and their positions in the cDNA-derived sequence. In the Table, positions without amino acid assignment are shown by "X;" uncertain positions are shown in parentheses. Peptides were obtained from Mac-1 purified on IB4 monoclonal antibody-Protein-A-Sepharose, except for peptide 86 that was obtained from Mac-1 purified on LM2/1 monoclonal antibody-Sepharose, and peptides 88 and 90 that were obtained from both sources. The peptide sequence used for the design of the oligonucleotide probe is underlined.

clones extending towards the N-terminus of the protein were selected. Isolation of the inserts of these 24 cDNA clones showed that three of them (λM23, λM42 and λM90) extend 2 kb 5' of λM14 (FIG. 1).

λM23 is a full-length Mac-1 α cDNA clone. It encodes the protein N-terminus (Miller, L. J. et al., *J. Immunol.*

TABLE I

SEQUENCES OF TRYPTIC PEPTIDES OF Mac-1 ALPHA-subunit

| Peptide | Amino Acid Sequence | Residues |
| --- | --- | --- |
| 14 | T I Q N Q L R | 307–313 |
| 32 | V Q S L V L G A P R | 400–409 |
| 43 | Y V I G V G D A F R | 267–276 |
| 44 | Y Q H I G L V A M F R | 410–420 |
| 53A | W Q C (D) A V L Y G E Q G Q P X G R | 488–504 |
| 53B | E F V (S) X X (M) (E) (Q) (L) | 155–164 |
| 54A | F (G) D P L G Y E D V I P E A D R | 246–261 |
| 71 | L F T A L F P F E K | 744–753 |
| 79A | V D S D M N D A Y L G (Y) | 379–390 |
| 79B | X Q (C) X I P F F G I Q E | 1015–1026 |
| 86 | G C P Q E D S D I A F L I D G S G S I I P H D F R | 127–151 |
| 88 | <u>T Q T V F F F P L D L S Y R</u> | 801–814 |
| 90 | L X F S L V G T P L S A F G N L R P V L A E D A Q R | 718–743 |

Peptide sequences were used to design 4 single sequence oligonucleotide probes. The peptide 88 was selected to design a 42-mer oligonucleotide specific for the α-subunit of Mac-1 because of its low level of redundancy and its homology to a region of the p150,95 α-subunit close to the C-terminus (i.e., towards the 3' end of a cDNA).

The oligonucleotides were end-labeled using T4 polynucleotide kinase and [$\gamma^{32}$P]-ATP (Maniatis, T., et al. (In: *Molecular Cloning, A Laboratory Manual,* Cold Spring Harbor Laboratories, Cold Spring Harbor, N.Y. (1982)) and used to screen a sized-selected cDNA library from PMA-induced HL60 cells (Corbi, A. et al., *EMBO J.* 6:4023–4028 (1987)). $5\times10^5$ primary recombinants were plated, transferred to duplicate nitrocellulose filters, and prehybridized overnight as described (Corbi, A. et al., *EMBO J.* 6:4023–4028 (1987)). Hybridization with the oligonucleotides was done in 6xSSC, 0.1% SDS, 0.05% sodium pyrophosphate, and 100 μg/ml of tRNA at 37° C. overnight. Filters were washed in the same solution without the tRNA at room temperature for 30 min. and at 45° C. for 15 minutes. Wet filters were exposed overnight to pre-flashed X-Ray film with intensifying screen.

Phage plaques giving duplicate positive signals were obtained after screening with a 42-mer oligonucleotide:

5'-ACCCAGGTGACCTTCTTCTTCCCCCTAGACCT GTCCTACCGG-3' and were subjected to three additional rounds of subcloning and screening with the same probe. Isolation of full-length cDNA clones was carried out by re-screening the filters with an end-labeled oligonucleotide having the sequence:

5'-GGATGGACTGGTAGACCTGACTGTAGGAGC-3' and nick-translated probes from the 5' end of the partial cDNA clone λM14.

The screening of the $5\times10^5$ primary recombinants from the PMA-induced HL-60 cDNA library with the 42-mer yield 16 positive clones and the longest one (λM14, 2.9 kb) was selected for sequencing (FIG. 1). The λM14 cDNA-derived amino acid sequence encodes four of the typtic peptides derived from the purified Mac-1 α-subunit. To isolate a full-length Mac-1 α cDNA clone, the library was re-screened with a 1.0 kb EcoRI fragment and a 30-mer derived from the 5' end of λM14 and twenty-four new cDNA 138:2381–2383 (1987)) and the tryptic peptides not detected in λM14. λM14 and λM23 exhibit identical restriction maps in their overlapping regions.

EXAMPLE 3

Restriction Mapping and Sequencing

DNA from the positive phages was purified, cloned into pUC13, 18 or 19, and restriction mapped using standard procedures (Maniatis, T., et al. (In: *Molecular Cloning, A Laboratory Manual,* Cold Spring Harbor Laboratories, Cold Spring Harbor, N.Y. (1982)). Restriction fragments were subcloned into M13 mp18 and mp19 and sequenced by the dideoxytermination method (Sanger, F. et al., *Proc. Natl. Acad. Sci. (U.S.A.)* 74:5463–5467 (1977). Oligonucletide-primed DNA sequencing was used in cases where no convenient restriction sites were available. The whole coding region, the 5' untranslated region and more than 60% of the 3' untranslated region were sequenced in both strands. The 3' untranslated regions of the cDNA clones λM23 and λM90 were subjected to dideoxy sequencing of plasmid DNA and using the Erase-a-base® system (Promega) to make deletions according to the manufacturer's instructions (Henikoff, S. Gene 28:351–359 (1984)).

The composite cDNA sequence of λM23 contains 4740 bp and has a long open reading frame of 3534 nucleotides, leaving a 5' untranslated region of 72 bp and a 3' untranslated region of 1.2 kb (FIG. 2). The 3' untranslated region of λM14 contains an inverted stretch of poly-(CA) (nucleotides 3667–3862) (Sun, L. et al., *Nucl. Acid Res.* 12:2669–2690 (1984)), a partial Kpn I interspersed repeat (nucleotides 4566–4631) (Sun, L. et al., *Nucl. Acid Res.* 12:2669–2690 (1984)), and ends with a stretch of more than 40 adenosines. There are 2 consensus polyadenylation signals at nucleotides 4191 and 4678. Analysis of the 3' untranslated regions from λM14, λM23, and λM90 indicates that the first polyadenylation signal is used in λM23 and the second one in λM14 and λM90, indicating that both polyadenylation signals are functional. Restriction mapping of 15 additional cDNA clones suggests that both polyadenylation sites are used with equal frequency. The 3' untranslated region of λM90 (and λM42) lack 440 bp found between nucleotides 3629 and 4070 in λM14 and λM23 (FIGS. 1). The sequences GAA/GTATCC and A<u>AG</u>/A at the boundaries of the deletion (arrows, FIG. 2) conform to the GT/AG rule for splicing sites (Mount, S. M., *Nucl. Acid Res.* 10:459–472 (1982)) and thus the two different classes of cDNA's appear to correspond to alternatively spliced mRNA's.

The open reading frame from λM14/λM23 translates into a protein of 1137 residues, with a signal peptide of 16 amino acids defined by the previously reported Mac-1 α-subunit N-terminal sequence (Miller, L. J. et al., *J. Immunol.* 138:2381–2383 (1987); Pierce, M. W. et al., *Biochim. Biophys. Acta* 874:368–372) (FIG. 2). In addition to the agreement with the protein N-terminal sequence, the 186 residues determined by tryptic peptide sequencing (Table I) agreed perfectly with the translated sequence. This confirmed the isolation of authentic Mac-1 α-subunit cDNA clones. The amino acid sequence of the Mac-1 α-subunit has the characteristics of a classical transmembrane protein, with an N-terminal 1092-residue domain, a 25-residue hydrophobic putative transmembrane domain, and a 19 residue C-terminal hydrophilic domain (FIG. 2). The presence in the N-terminal 1092-residue domain of 19 potential N-glycosylation sites (Asn-Xaa-Ser/Thr), one of which was sequenced in peptide 90 (residues 718–743), confirms that this is the extracellular domain. The predicted molecular weight of the protein is 125,611 daltons, consistent with previous estimations after N-glycanase treatment of the α-subunit of Mac-1 (137,000 Mr) (Miller, L. J. et al., *J. Immunol.* 139:842–847 (1987)). Assuming 2,500 Mr per high mannose carbohydrate, Mr=173,001 is predicted for the Mac-1 α-subunit precursor, compared to the observed M=160,000 (Miller, L. J. et al., *J. Immunol.* 139:842–847 (1987)). After carbohydrate processing, the Mac-1 α-subunit is 170,000 Mr.

The primary structure of the α-subunit of Mac-1 suggests the presence of seven internal repeats (FIG. 3). Repeats V, VI, and VII show the highest degree of similarity to one another which is statistically significant ($p<10^{-2}$ to $p<10^{-4}$) and contain sequences similar to the divalent cation-binding EF-hand loop motif of proteins like calmodulin and parvalbumin (Szebenyi, D. M. E. et al., *Nature* 294:327–332 (1981)) (FIG. 3), correlating with the divalent cation requirements of the Mac-1-mediated adhesion (Wright, S. D. et al., *Proc. Natl. Acad. Sci.* (*U.S.A.*) 80:5699–5703 (1983)). Repeats I–IV lack the EF-hand loop-like sequences but contain the highly conserved sequences Y F G A S/A L and L V T V G A P flanking the center of the repeats (FIG. 3). These consensus flanking sequences are also conserved in other integrins (FIG. 3). The presence of the seven repeats suggest that much of the N-terminal portion of the Mac-1 α-subunits may have arisen by duplication events.

EXAMPLE 4

Northern Blot Analysis

Adherent mononuclear cells from peripheral blood were isolated by Ficoll-Hypaque centrifugation and incubation of the mononuclear cells in tissue culture plates with RPMI 1640 and 10% fetal calf serum for 30 min. at 37° C. Non-adherent cells were removed from the plates by extensive washing with RPMI 1640. Adherent cells were detached from the plates by incubation with 10 ml of PBS, 5 mM EDTA, for 15 minutes at 37° C. More than 95% of the adherent cells were positive for the presence of Mac-1 as detected by indirect immunofluorescence. PMA-treatment of the cell lines HL-60 and U937 was performed as described (Miller, L. J. et al., *J. Immunol.* 137:2891–2900 (1986)). total RNA was extracted from peripheral blood adherent cells, as well as from the cell lines SKW3, JY, HL-60, and U937, using guanidine isothiocyanate (Maniatis, T., et al. (In: *Molecular Cloning, A Laboratory Manual,* Cold Spring Harbor Laboratories, Cold Spring Harbor, N.Y. (1982)). 10 or 20 μg from each sample was run on a 1% formaldehyde-agarose gel and transferred onto a nylon membrane. Hybridizations were performed using the 2.3 kb Eco RI fragment from λM23 as a probe.

The cell surface expression of the Mac-1 α/β complex was found to be almost exclusively restricted to cells of the myeloid lineage (Miller, L. J. et al., *J. Immunol.* 137:2891–2900 (1986)). Northern blots showed that the Mac-1 α-subunit mRNA is 4.7 kb and was present in monocytes and myeloid cell lines, but not in T or B cell lines.

Mac-1 expression was regulated during leukocyte differentiation, and could be induced in myelomonoctic cell lines by culture with phorbol ester for 1–3 days (Miller, L. J. et al., *J. Immunol.* 137:2891–2900 (1986)). Northern blot analysis revealed that the steady-state level of Mac-1 α RNA in the HL-60 and U937 mylelomonocytic cell lines was extremely low or nil (Miller, L. J. et al., *J. Immunol.* 137:2891–2900 (1986)). PMA-treatment of both cell lines induced expression of the Mac-1 α-subunit mRNA and increased the expression of the β-subunit mRNA. These findings are concordant with previous studies on the biosynthesis of the Mac-1 α and β-subunits (Miller, L. J. et al., *J. Immunol.* 139:842–847 (1987)), on the surface expression of the Mac-1 α/β complex on these cell lines (Miller, L. J. et al., *J. Immunol.* 137:2891–2900 (1986)), and suggest that the cell surface expression of Mac-1 is regulated by mRNA level. Similarly, treatment of the murine premyelocytic cell line M1 with γ-interferon induces expression of the muring Mac-1 α-subunit mRNA (Sastre, L. et al., *Proc. Natl. Acad. Sci.* (*U.S.A.*) 83:5644–5648 (1986)). Two Mac-1 α-subunit messages of approximately 4.7 and 4.4 kb were resolved in the myelomonocytic cell lines HL60 and U937 upon prolonged electrophoresis of the RNA. The presence of multiple Mac-1 α mRNA species may be the result of the alternative use of the two polyadenylation signals or alternative splicing. The size of the mRNA species is consistent with these possibilities. Southern blot analysis under stringent conditions on human DNA demonstrated that Mac-1 α-subunit is encoded by a single copy gene.

EXAMPLE 5

Sequence Homologies

The sequence of Mac-1 α-subunit was compared with the protein sequence database in the National Biomedical Research Foundation (NBRF) (Washington, D.C.). The ALIGN program was used for alignment of sequences (Dayhoff, M. O. et al., *Met. Enzymol.* 91:524–545 (1983)). The statistical significant of the alignments was assessed obtaining the alignment scores for 100 random permutations of the aligned sequences and calculating the number of standard deviations between the mean of the scores for the randomized comparisons and the score of the actual alignment. The scoring used the 250 PAM mutation data matrix, with a gap penalty=6 and a bias=6.

EXAMPLE 6

Mac-1 as a Member of the Integrin Gene Superfamily

The determination of the primary structure of the Mac-1/LFA-1/p150,95 common β-subunit (Kishimoto, T. K. et al., *Cell* 48:681–690 (1987); Law, S. K. A. et al., *EMBO J.* 6:915–919 (1987)) and the α-subunit of p150,95 (Corbi, A. et al., *EMBO J.* 6:4023–4028 (1987)) has shown that the leukocyte adhesion receptors are evolutionary related to the extracellular matrix (ECM) receptors, and led to the concept of a gene superfamily of cell-cell and cell-matrix receptors termed "integrins" (Hynes, R. O. *Cell* 48:549–554 (1987)).

Three subfamilies of integrin molecules, each with a distinct β-subunit, have been defined, namely the fibronectin receptor subfamily (sharing integrin $β_1$), the leukocyte adhesion receptor subfamily (sharing integrin $β_2$), and the vitronectin receptor-IIb/IIIa subfamily (sharing integrin $β_3$).

Comparisons of the amino acid and nucleic acid sequences which encode the integrins with those of the Mac-1 α-subunit were undertaken to define the relationships among the α-subunits of the different integrin subfamilies (FIG. 4). The α-subunits of Mac-1 and p150,95 were found to be 63% identical at the amino acid level and 68% identical at the nucleotide level. The high degree of structural similarity between the α-subunits of Mac-1 and p150,95 is reflected at the functional level: Mac-1 and p150,95 exhibit iC3b-binding ability (Beller, D. I. et al., *J. Exper. Med.* 156:1000–1009 (1982); Micklem, K. J. et al., *Biochem. J.* 231:233–236 (1985)) and both proteins are known to play a role in neutrophil aggregation and neutrophil and monocyte adhesion to endothelials cells (Anderson, D. C. et al., *J. Immunol.* 137:15–27 (1986); Vedder, N. B. et al., *J. Clin. Invest.* 81:672–682 (1988); Te Velde, A. A. et al., *Immunol.* 61:261–267 (1987)). The α-subunit of LFA-1 is 35% identical to the α-subunits of Mac-1 and p150,95. The α-subunits of the fibronectin receptor, vitronectin receptor and the glycoprotein IIb are 40% identical to one another. Since the α-subunits of Mac-1 and p150,95 are 25% identical to the α-subunits of the three ECM receptors, the α-subunits of Mac-1, P150,95, and LFA-1 are more closely related to each other than to the rest of the integrin α-subunits. The leukocyte α-subunits also resemble one another in containing a segment of 187 residues not found in the ECM α-subunits (amino acids 150–338 in the α-subunit of Mac-1), and in lacking a region of 28 amino acids (gap at residue 1002 in Mac-1) where the ECM receptor α-subunits are proteolytically cleaved during processing to generate two disulfide-linked chains (Ruoslahti, E. et al., *Science* 238:491–497 (1987)).

The area of highest extended identity between Mac-1 α-συβυνιτ and the rest of the integrin α-subunits lies between residues 434–592, precisely the boundaries of the three internal repeats containing putative divalent cation-binding sequences. Over this region, Mac-1 α-subunit shows 88% identity to p150,95 α-subunit at the amino acid level and 90% at the nucleotide level, and the percentage of identity to the ECM receptor integrin α-subunits is 38%. The ECM receptor α-subunits have four putative divalent cation-binding sites within their primary structure (Suzuki, S. et al., *J. Biol. Chem.* 262:14080–14085 (1987); Argraves, W. S. et al., *J. Cell Biol.* 105:1183–1190 (1987); Poncz, M. et al., *J. Biol. Chem.* 262:8476–8482 (1987)), which align with the repeats IV–VII in the α-subunits of Mac-1 and p150,95; repeat IV in Mac-1 and p150,95 does not contain the putative divalent cation-binding sequence (FIG. 3). Ligand-binding by the ECM receptor integrins is calcium-dependent (Ruoslahti, E. et al., *Science* 238:491–497 (1987)) and in the case of the α-subunit of the glycoprotein IIb/IIIa the binding of radioactive calcium has been verified (Ruoslahti, E. et al., *Science* 238:491–497 (1987)). The high degree of conservation of these regions suggests a role in maintaining receptor conformation or a direct involvement in ligand binding.

An additional region of high conservation among the integrin α-subunits are the membrane spanning regions. The transmembrane domain of Mac-1 α exhibits 88% identity with the one in p150,95 α and 40–50% identity with those of the IIb, VNR and FNR α-subunits (Tamkun, J. W. et al., *Cell* 46:271–282 (1986); Argraves, W. S. et al., *J. Cell Biol.* 105:1183–1190 (1987); Poncz, M. et al., *J. Biol. Chem.* 262:8476–8482 (1987)) (FIG. 4). A similar conservation has been noted in the transmembrane and cytoplasmic domains of the different β-subunits (Kishimoto, T. K. et al., *Cell* 48:681–690 (1987); Law, S. K. A. et al., *EMBO J.* 6:915–919 (1987)); Tamkun, J. W. et al., *Cell* 46:271–282 (1986); Fitzgerald, L. A. et al., *J. Biol. Chem.* 262:3936–3939 (1987); Argraves, W. S. et al., *J. Cell Biol.* 105:1183–1190 (1987)). Based on this high degree of conservation it is conceivable that these regions may play a role in the regulation of the ligand-binding (Vedder, N. B. et al., *J. Clin. Invest.* 81:672–682 (1988)) through interactions with other membrane components or with the cytoskeleton. The finding that the fibronectin receptor binds talin (Horwitz, A. et al., *Nature* 320:531–533 (1986)), that LFA-1 mediated interactions are dependent on the integrity of the cytoskeleton (Springer, T. A. et al., *Ann. Rev. Immunol.* 5:223–252 (1987)), and that LFA-1 co-caps with talin after phorbol ester stimulation (Burn, P. et al., *Proc. Natl. Acad. Sci. (U.S.A.)* 85:497–501 (1988)) further supports the involvement of these domains in cytoskeletal interactions and in signal tranduction.

EXAMPLE 7

Mapping of the Mac-1 Alpha Gene

The Mac-1, LFA-1, and p150,95 α and β-subunit genes have been located by Southern blot on mouse×human somatic cell hybrids and by chromosomal in situ hybridization using cDNA probes. The genes encoding the α-subunits of LFA-1, Mac-1 and p150,95 map to chromosome 16, between bands p11–p13.1, defining a gene cluster involved in leukocyte adhesion. The common structural characteristics and the close proximity of the three α-subunit genes strongly suggest that the genes for the α-subunits of Mac-1, p150,95, and LFA-1 evolved by gene duplication events, and that these gene duplications took place after the divergence of the different integrin α-subunit subfamilies.

EXAMPLE 8

Homology with Von Willebrand Factor and Factor B

Figure 6:
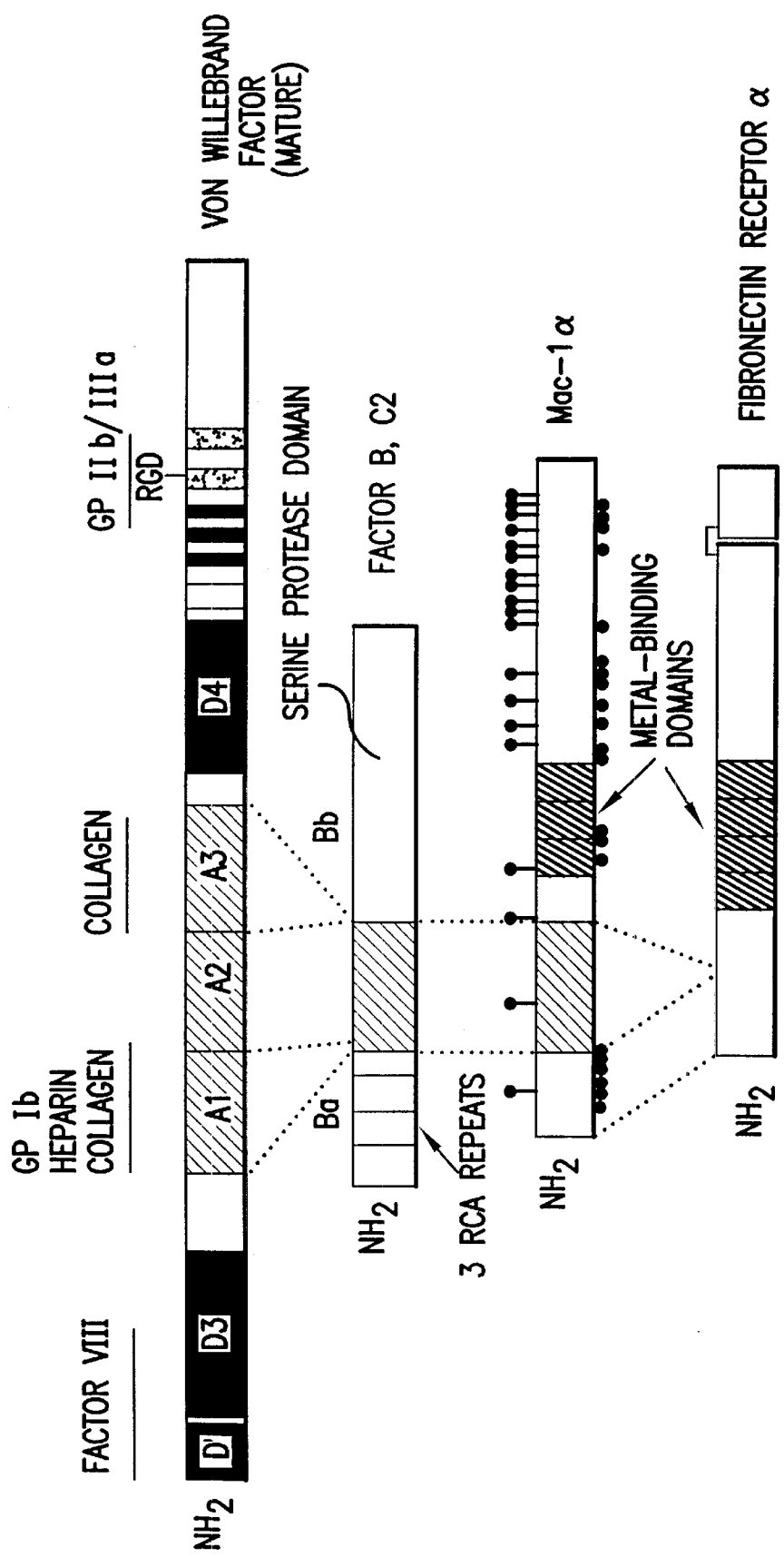
FIG. 6 shows the proposed evolutionary relationsips of the Mac-1 α-subunit, the A domains of von Willebrand factor, factor B and C2. The binding domains and the ligands for von Willebrand factor are indicated on top (Shelton-Inloes, B. B. et al., *Biochem.* 25:3164–3171 (1986); Girma, J. P. et al., *Blood* 70:605–611 (1987)). The structures of factor B and C2 are as previously described (Mole, J. E. et al., *J. Biol. Chem.* 259:3407–3412 (1984); Bentley, D. R., *Biochem. J.* 239:339–345 (1986)) were also examined. RCA (Regulator of complement activation) repeats in factor B and C2 are 60 amino acids homologous repeats common to many complement components and receptors. The N-glycosylation sites and the cysteine residues in the α-subunit of Mac-1 are shown on top and bottom of its schematic representation, respectively.

As previously described for p150,95 (Corbi, A. et al., *EMBO J.* 6:4023–4028 (1987)), there is a region of 187 amino acids in the Mac-1 α-subunit (resides 150–338) without counterpart in the 3 sequenced ECM receptor integrin α-subunits. This region is referred to as the L domain, because of its presence in leukocyte integrins. The above discussed search of the National Biomedical Research Foundation sequence data base using the FASTP program revealed homology of residues 128–314 of the Mac-1 α-subunit with von Willebrand factor (vWF) (Shelton-Inloes, B. B. et al., *Biochem.* 25:3164–3171 (1986)) (FIG. 5). The homologous regions are of particular interest because they correspond in Mac-1 almost exactly to the L domain, and in vWF to the type A domain, a domain previously defined by its presence in 3 homologous tandem repeats of 200 residues denoted A1 (497–716), A2 (717–909), and (910–1111) (Shelton-Inloes, B. B. et al., *Biochem.* 25:3164–3171 (1986)). The p150,95 α-subunit (FIG. 4) and the murine Mac-1 α-subunit also show homology to the vWF A domains. Since the vWF A domains have previously have shown to be homologous to factor B (Shelton-Inloes, B. B. et al., *Biochem.* 25:3164–3171 (1986); Mole, J. E. et al., *J. Biol. Chem.* 259:3407–3412 (1984)), a component of the alternative complement pathway which interacts with C3, homologies with factor B and with its homologue in the classical pathway, C2 (Bentley, D. R., *Biochem. J.* 239:339–345 (1986)) were also examined (FIG. 5). The homologous domain in factor B is clearly demarcated on the N-terminal side by the site at which factor B is cleaved to give the active Bb factor, and on the C-terminal side by the serine protease domain (Mole, J. E. et al.,*J. Biol. Chem.* 259:3407–3412 (1984)); Bentley, D. R., *Biochem. J.* 239:339–345 (1986)) (FIG. 6). Evaluation with the ALIGN program (Dayhoff, M. O. et al., *Met. Enzymol.* 91:524–545 (1983)) showed that the homology of Mac-1 with vWF domains A1, A2, and A3 and with factor B is highly statistically significant (Table II), and, thus, that the homologous amino acid segments in each of these proteins must have evolved from a single primordial domain. Although the homology of Mac-1 with C2 is not statistically significant, factor B shows significant homology to C2 and serves as an evolutionary link, showing that the segment in C2 evolved from the same primordial domain. Table II compares the alignment scores of the Mac-1 alpha-subunit leukocyte specific domain (128–314), with the A repeats of von Willebrand factor (A1:509–692; A2:730–903; A3:923–1103), Factor B (240–443), and C2 (228–434). The table was compiled using the ALIGN program. The alignment scores are presented in standard deviation units. The probability of the alignments (shown in FIG. 6) have occurred by chance is shown in parentheses below each alignment score.

TABLE II

SIGNIFICANCE OF THE ALIGNMENT SCORES OF THE Mac-1 ALPHA-subunit LEUKOCYTE-SPECIFIC DOMAIN WITH THE von WILLEBRAND FACTOR A REPEATS, FACTOR B AND C2

|        | vWf A1 | vWf A2 | vWf A3 | Factor B | C2 |
|--------|--------|--------|--------|----------|-----|
| Mac-1  | 7.4 ($<10^{-11}$) | 7.2 ($<10^{-11}$) | 8.1 ($<10^{-15}$) | 6.9 ($<10^{-10}$) | 1.8 ($<10^{-1}$) |
| vWf A1 | —      | 10.3 ($<10^{-23}$) | 9.1 ($<10^{-18}$) | 7.0 ($<10^{-11}$) | 4.6 ($<10^{-5}$) |
| vWf A2 | —      | —      | 13.4 ($<10^{-23}$) | 4.0 ($<10^{-4}$) | 4.1 ($<10^{-4}$) |
| vWf A3 | —      | —      | —      | 4.8 ($<10^{-5}$) | 3.2 ($<10^{-2}$) |
| Factor B | —    | —      | —      | —        | 23.8 ($<10^{-23}$) |

EXAMPLE 9

The Ligand Binding Site of the Mac-1 Alpha-subunit

The homology between factor B and the L domain, and the ability of factor B to bind C3b, support the conclusion that the L domain is the iC3b ligand-binding site of Mac-1 and p150,95. It is also of interest that binding of Bb to C3b requires $Mg^{+2}$ (Muller-Eberhard, H. J. et al., *Adv. Immunol.* 29:1–53 (1980)). Similarly, binding of isolated Mac-1 and p150,95 to iC3b-sensitized cells or to iC3b-Sepharose requires divalent cations (Wright, S. D. et al., *Proc. Natl. Acad. Sci.* (*U.S.A.*) 80:5699–5703 (1983); Micklem, K. J. et al., *Biochem. J.* 231:233–236 (1985)). A putative divalent cation binding site in the L domain may be represented by one sequence motif containing dG and another containing DG and GD which are concerned in Mac-1, p150,95, and factor B (underlined in FIG. 5). If these sites were contiguous in the 3 dimensional structure they could form a divalent cation binding site similar in sequence to those present in internal repeats V to VII of the α-subunit of Mac-1. The L domain and the following region containing repeats IV–VII are relatvely free of N-linked glycosylation sites and cysteines (FIG. 6), allowing them to be accessible and conformationally flexible. The idea that the L domain could be involved in recognition of iC3b raises the possibility of recognition of a sequence in iC3b distinct from RGD. Although RGD is present in iC3b, evidence that it is important in recognition by Mac-1 (Wright, S. D. et al., *Proc. Natl. Acad. Sci.* (*U.S.A.*) 84:1965–1968 (1987)) remains to be confirmed by peptide inhibition data.

Both the A1 and A3 domains of vWF bind collagen (Girma, J. P. et al., *Blood* 70:605–611 (1987)) and the A1 domain binds the platelet glycoprotein Ib and heparin (Girma, J. P. et al., *Blood* 70:605–611 (1987)). The alternative complement pathway in which factor B plays an important role is the most primitive mechanism of the immune system for distinguishing self from non-self (Muller-Eberhard, H. J. et al., *Adv. Immunol.* 29:1–53 (1980)). Thus, the 200 amino acid domain appears to be a primitive recognition unit which has been duplicated and embedded in a number of proteins which have evolved to play diverse recognition functions in hemostasis (vWF), the extracellular matrix (CMP) complement activation (factor B and C2), and complement receptor and cell-cell interactions (leukocyte integrins).

EXAMPLE 10

The Phylogenetic Relationship Between the Integrins

The ECM receptor integrins are phylogenetically ancient as shown at the level of sequence homology in Drosophila (Ruoslahti, E. et al., *Science* 238:491–497 (1987)) and by immunological cross-reaction with proteins of similar size in nematodes and fungi. These results demonstrate that the Mac-1 α-subunit evolved by the introduction of a primordial recognition domain into the ECM receptor-type of α-subunit evolved by the introduction of a primordial recognition domain into the ECM receptor-type of α-subunit (FIG. 6). The introduction of the extra domain may have increased the potential for recognition of diverse ligands by the leukocyte integrins and may explain their somewhat different ligand specificity, since recognition of the ICAM-1 ligand by LFA-1 does not involve RGD (Marlin, S. et al., *Cell* 51:813–819 (1987); Staunton, D. E. et al., *Cell* 52:925–933 (1988); Simmons, D. et al., *Nature* 331:624–627 (1988), all of which references are incorporated herein by reference).

The availability of cDNA clones for both the α and β-subunits of Mac-1 allows the identification of the distinct ligand binding sites involved in iC3b binding and in cell-cell adhesion, and the testing of the hypothesis that cell stimulation results in a conformational change in the ligand binding site, transmitted from the cytoplasmic or membrane domains, that alters affinity for ligand.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A polypeptide consisting of amino acids 150 to 338 of FIG. 2.

2. A polypeptide consisting of amino acids 434 to 592 of FIG. 2.

3. The polypeptide of claim 1 produced by expression of a recombinant DNA molecule encoding said polypeptide in a transformed cell.

4. The polypeptide of claim 2 produced by expression of a recombinant DNA molecule encoding said polypeptide in a transformed cell.

* * * * *